United States Patent
Marino

(10) Patent No.: US 6,290,724 B1
(45) Date of Patent: Sep. 18, 2001

(54) METHODS FOR SEPARATING AND STABILIZING ADJACENT VERTEBRAE

(75) Inventor: James F. Marino, La Jolla, CA (US)

(73) Assignee: Nuvasive, Inc., San Diego, CA (US)

( * ) Notice: Subject to any disclaimer, the term of this patent is extended or adjusted under 35 U.S.C. 154(b) by 0 days.

(21) Appl. No.: 09/320,161

(22) Filed: May 26, 1999

Related U.S. Application Data

(60) Provisional application No. 60/086,945, filed on May 27, 1998, provisional application No. 60/113,651, filed on Dec. 23, 1998, and provisional application No. 60/120,663, filed on Feb. 19, 1999.

(51) Int. Cl.$^7$ .................................................. A61F 2/44
(52) U.S. Cl. .......................................................... 623/17.11
(58) Field of Search .............................. 623/17.11, 17.16

(56) References Cited

U.S. PATENT DOCUMENTS

| | | |
|---|---|---|
| 3,745,995 | 7/1973 | Kraus . |
| 3,848,601 | 11/1974 | Ma et al. . |

(List continued on next page.)

FOREIGN PATENT DOCUMENTS

| | | |
|---|---|---|
| 2015507 | 6/1991 | (CA) . |
| 0706876 | 4/1996 | (EP) . |
| 0716840 | 6/1996 | (EP) . |
| 0517030 | 9/1996 | (EP) . |
| 0737448 | 10/1996 | (EP) . |
| 0796593 | 9/1997 | (EP) . |
| 0809974 | 12/1997 | (EP) . |
| 0809975 | 12/1997 | (EP) . |
| 0811356 | 12/1997 | (EP) . |
| 0369603 | 5/1998 | (EP) . |
| 880938 | 12/1998 | (EP) . |

(List continued on next page.)

OTHER PUBLICATIONS

Kambin et al., "History and current status of percutaneous arthroscopic disc surgery" *Spine* (1996) 21(24S):57S–61S.

Cargill et al., "Current and future approaches to lumbar disc surgery: A literature review" *Medscape Orthopedics & Sports Medicine*, http:///www.medscape.com/Medscape/OrthoSportsMed/1997/v01.n11/m.../mos3057.alleyne.html (printed from World Wide Web: Mar. 15, 1998) 20 pages total.

McCord et al., "Anterior endoscopic thoracolumbar instrumentation" AcroMed® Corporation, 3303 Carnegie Avenue, Cleveland, OH, 44115 (1996) pp. 1–16.

*Primary Examiner*—Jeffrey A. Smith
(74) *Attorney, Agent, or Firm*—Townsend and Townsend and Crew LLP

(57) ABSTRACT

A method for separating and stabilizing adjacent vertebrae (50 and 52), comprising: introducing insert (20) between vertebrae (50 and 52); rotating insert (20) to engage cam surfaces (32 and 34) thereon against vertebrae (50 and 52) to move vertebrae (50 and 52) apart; and anchoring insert (20) between vertebrae (50 and 52).

A posterolateral and percutaneous method of separating and stabilizing adjacent vertebrae (50 and 52), comprising: percutaneously introducing a first insert (19a) and a second insert (19b) between adjacent vertebrae (50 and 52) with rotational axes (26a and 26b) of insert (19a) and 19b) being at a generally right angle to one another.

An intervertebral insert (20) comprising a body having a posterior end (22), an anterior end (24), a rotational axis (26) between ends (22 and 24), and a pair of outwardly facing convexly curved surfaces (32 and 34) which are disposed generally parallel to rotational axis (26) and which are adapted to engage and separate opposed vertebral surfaces (50 and 52) when insert (20) is placed between adjacent vertebrae (50 and 52) and rotated.

28 Claims, 23 Drawing Sheets

U.S. PATENT DOCUMENTS

| | | |
|---|---|---|
| 4,026,304 | 5/1977 | Levy . |
| 4,781,591 | 11/1988 | Allen . |
| 4,877,020 | 10/1989 | Vich . |
| 4,932,975 | 6/1990 | Main et al. . |
| 4,961,740 | 10/1990 | Ray et al. . |
| 5,026,373 | 6/1991 | Ray et al. . |
| 5,055,104 | 10/1991 | Ray . |
| 5,062,845 | 11/1991 | Kuslich et al. . |
| 5,133,717 | 7/1992 | Chopin . |
| 5,171,278 | 12/1992 | Pisharodi . |
| 5,290,494 | 3/1994 | Coombes et al. . |
| 5,300,076 | 4/1994 | Leriche . |
| 5,304,210 | 4/1994 | Crook . |
| 5,306,307 | 4/1994 | Senter et al. . |
| 5,306,309 | 4/1994 | Wagner et al. . |
| 5,334,205 | 8/1994 | Cain . |
| 5,336,223 | 8/1994 | Rogers . |
| 5,364,400 | 11/1994 | Rego, Jr. et al. . |
| 5,395,372 | 3/1995 | Holt et al. . |
| 5,397,363 | 3/1995 | Gelbard . |
| 5,413,602 | 5/1995 | Metz-Stavenhagen . |
| 5,425,772 | 6/1995 | Brantigan . |
| 5,431,658 * | 7/1995 | Moskovich .............................. 606/99 |
| 5,443,514 | 8/1995 | Steffee . |
| 5,443,515 | 8/1995 | Cohen et al. . |
| 5,445,639 | 8/1995 | Kuslich et al. . |
| 5,454,811 | 10/1995 | Huebner . |
| 5,458,638 | 10/1995 | Kuslich et al. . |
| 5,489,308 | 2/1996 | Kuslich et al. . |
| 5,522,879 | 6/1996 | Scopelianos . |
| 5,522,899 | 6/1996 | Michelson . |
| 5,524,624 | 6/1996 | Tepper et al. . |
| 5,534,030 | 7/1996 | Navarro et al. . |
| 5,540,688 | 7/1996 | Navas . |
| 5,562,736 | 10/1996 | Ray et al. . |
| 5,565,005 | 10/1996 | Erickson et al. . |
| 5,571,192 | 11/1996 | Schönhöffer . |
| 5,593,409 | 1/1997 | Michelson . |
| 5,609,636 | 3/1997 | Kohrs et al. . |
| 5,611,800 | 3/1997 | Davis et al. . |
| 5,645,598 | 7/1997 | Brosnahan, III . |
| 5,653,761 | 8/1997 | Pisharodi . |
| 5,653,762 | 8/1997 | Pisharodi . |
| 5,658,336 | 8/1997 | Pisharodi . |
| 5,658,337 | 8/1997 | Kohrs et al. . |
| 5,665,122 | 9/1997 | Kambin . |
| 5,669,909 | 9/1997 | Zdeblick et al. . |
| 5,676,703 | 10/1997 | Gelbard . |
| 5,683,394 | 11/1997 | Rinner . |
| 5,683,464 | 11/1997 | Wagner et al. . |
| 5,690,629 | 11/1997 | Asher et al. . |
| 5,700,264 | 12/1997 | Zucherman et al. . |
| 5,700,291 | 12/1997 | Kuslich et al. . |
| 5,700,292 | 12/1997 | Margulies . |
| 5,702,449 | 12/1997 | McKay . |
| 5,702,451 | 12/1997 | Biedermann et al. . |
| 5,702,453 | 12/1997 | Rabbe et al. . |
| 5,711,957 | 1/1998 | Patat et al. . |
| 5,716,415 | 2/1998 | Steffee . |
| 5,720,748 | 2/1998 | Kuslich et al. . |
| 5,720,751 * | 2/1998 | Jackson .................................. 606/86 |
| 5,766,252 | 6/1998 | Henry et al. . |
| 5,772,661 | 6/1998 | Michelson . |
| 5,782,919 * | 7/1998 | Zdeblick et al. .................. 623/17.16 |
| 5,785,710 | 7/1998 | Michelson . |
| 5,797,909 | 8/1998 | Michelson . |
| 5,800,549 * | 9/1998 | Bao et al. . |
| 5,800,550 | 9/1998 | Sertich . |
| 5,814,084 | 9/1998 | Grivas et al. . |
| 5,885,299 | 3/1999 | Winslow et al. . |
| 5,888,224 | 3/1999 | Beckers et al. . |
| 5,893,890 | 4/1999 | Pisharodi . |
| 5,904,719 * | 5/1999 | Errico et al. ....................... 623/17.16 |
| 5,910,315 * | 6/1999 | Stevenson et al. .................. 424/422 |
| 5,968,098 | 10/1999 | Winslow . |
| 6,004,326 | 12/1999 | Castro et al. . |
| 6,015,436 | 1/2000 | Schonhoffer . |
| 6,033,405 | 3/2000 | Winslow et al. . |
| 6,042,582 | 3/2000 | Ray . |
| 6,063,088 | 5/2000 | Winslow . |
| 6,083,225 | 7/2000 | Winslow et al. . |
| 6,102,948 | 8/2000 | Brosnahan, III . |
| 6,120,506 | 9/2000 | Kohrs et al. . |

FOREIGN PATENT DOCUMENTS

| | | |
|---|---|---|
| WO 91/06261 | 5/1991 | (WO) . |
| WO 94/04100 | 3/1994 | (WO) . |
| WO 94/10928 | 5/1994 | (WO) . |
| WO 95/01810 | 1/1995 | (WO) . |
| WO 96/08205 | 3/1996 | (WO) . |
| WO 96/17564 | 6/1996 | (WO) . |
| WO 96/41582 | 12/1996 | (WO) . |
| WO 97/20513 | 6/1997 | (WO) . |
| WO 97/33525 | 9/1997 | (WO) . |
| WO 97/37620 | 10/1997 | (WO) . |
| WO 98/09586 | 3/1998 | (WO) . |
| WO 98/14142 | 4/1998 | (WO) . |
| WO 98/17208 | 4/1998 | (WO) . |
| WO 99/08627 | 2/1999 | (WO) . |
| WO 99/38461 | 8/1999 | (WO) . |

* cited by examiner

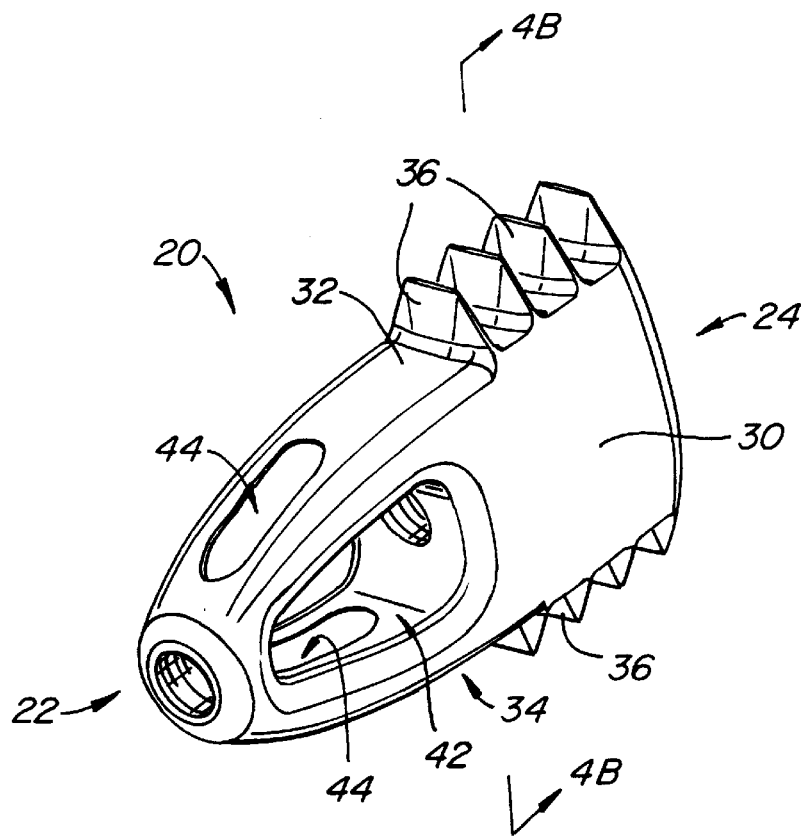
FIG. IA.
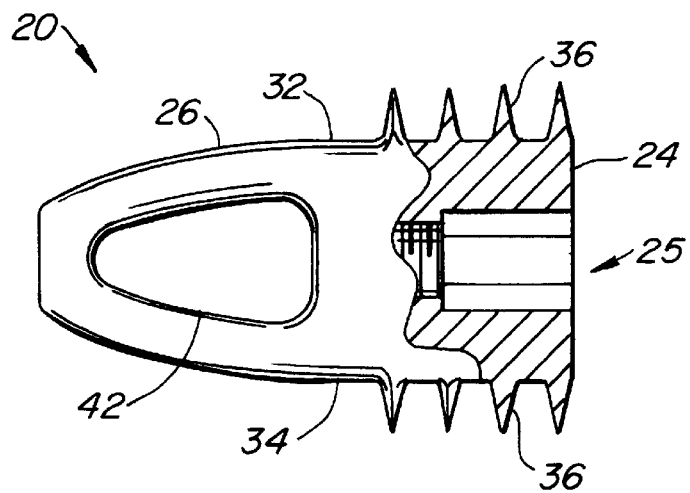
FIG. 2.

METHODS FOR SEPARATING AND STABILIZING ADJACENT VERTEBRAE

CROSS-REFERENCES TO RELATED APPLICATIONS

The present application is a regular application of U.S. Provisional Patent Application Ser. No. 60/086,945 filed May 27, 1998; U.S. Provisional Patent Application Ser. No. 60/113,651 filed Dec. 23, 1998; and U.S. Provisional Patent Application Ser. No. 60/120,663 filed Feb. 19, 1999; the complete disclosure of which are hereby incorporated herein by reference for all purposes.

TECHNICAL FIELD

The present invention relates to systems for separating and stabilizing adjacent vertebrae.

BACKGROUND OF THE INVENTION

Intervertebral spinal inserts are used to provide support and maintain normal distance between adjacent vertebrae in cases where a patient's vertebral discs have degenerated. Such degeneration can occur as a result of aging or trauma and typically results in pinched or damaged nerves between or proximal to the adjacent vertebrae. Moreover, such discal degeneration causes shifting of the loading along the patient's spinal column, which in turn further accelerates the vertebral degeneration.

Intervertebral inserts are typically used to reestablish normal intervertebral spacing, stabilize and reduce bone motion and, in conjunction with graft matter, to cause fusion between adjacent vertebral bodies.

A common problem with existing intervertebral inserts is that their insertion into the patient's spine is usually accomplished by invasive open surgical procedures. Such invasive surgery can be performed by entering either through the patient's back or through the abdomen. A major disadvantage of such invasive surgery is that it requires a considerable post-operative recovery time for the patient.

Another disadvantage is that, during such major surgery, the actual insertion of the intervertebral insert requires distraction of the adjacent vertebrae to first open a sufficiently large passage for the insertion of the insert therebetween. Such distraction is typically performed by dedicated instrumentation and invasive tools which must first enter the intervertebral space and then grip and hold apart the adjacent vertebrae.

A related disadvantage of current surgical methods of inserting intervertebral inserts is that they require cutting through, scarring and damaging either the posterior longitudinal ligament or the anterior longitudinal ligament, the facet joint capsules, interspinous ligaments and other paraspinal tissues. This reduces the amount of natural tension between the relevant vertebrae which reduces spinal column stability and may allow the inserts to move from their desired location.

An additional problem with the insertion of current intervertebral inserts is the requirement that portions of the adjacent vertebrae have to be drilled, chiseled away or otherwise removed to accommodate the particular geometric shape and orientation of the insert. Accordingly, in addition to the requirement of distracting the adjacent vertebrae, current systems typically also require drilling or chiseling away of the hard exterior surface of the vertebral endplates so that the insert can be received therein. This removal of the hard exterior endplate surface exposes the softer cancellous bone which is not sufficiently strong to bear the required load. Accordingly, the subsequent insertion of a typical metal cage-type insert into this softer cancellous portion of the vertebral bone requires the spinal load to be directed against a weaker supporting surface. A danger exists that such inserts may fail in their purpose of maintaining intervertebral spacing because they sink into softer bone.

Moreover, the shape of current inserts does not take advantage of the natural contoured shape of the adjacent vertebral surfaces such that an intervertebral insert can be provided which supports itself flush against the contour of the vertebral surfaces with the vertebrae being supported at a proper lordotic angle.

An additional problem with many current insert designs is that they often do not adequately promote or provide an opportunity for bone growth therethrough so as to firmly embed the insert within the spine over time.

SUMMARY OF THE INVENTION

The present invention provides methods for separating and stabilizing adjacent vertebrae as well as providing intervertebral inserts, systems and kits for use in performing these methods.

A method for separating and stabilizing adjacent vertebrae comprises introducing an insert between the vertebrae and rotating the insert to engage outwardly facing convexly curved camming surfaces thereon against the vertebrae thereby moving the vertebrae apart. As will be explained, an advantage of camming the vertebrae apart with such outwardly facing convexly curved camming surfaces is that side-to-side vertebral motion is minimized such that the adjacent vertebrae do not tend to move horizontally with respect to one another as they are cammed apart in a vertical direction.

In various preferred aspects of the invention, the insert can either be inserted temporarily (such as during a surgical procedure) or permanently (so as to provide long term intervertebral stabilization). In those aspects where the insert is to remain in position permanently, methods for anchoring the insert firmly between the adjacent vertebrae are provided. When the insert is rotated into position, it then supports the spinal load, and distracts the adjacent vertebrae. This tensions the intervertebral ligaments and can decompress neurological elements. Using the present methods, prior distraction of the adjacent vertebrae with dedicated instrumentation is either not required, or is substantially minimized.

In a preferred aspect, the insert is inserted into the patient's intervertebral space in a percutaneous, posterolateral fluoroscopically guided approach. Preferably, the posterolateral approach is made at an angle in the range of 35 to 90 degrees, and most preferably 45°, from the sagittal plane of the patient. Such an approach avoids and thus helps preserve the ligamentous structures which holds the vertebrae together, in particular, the anterior and posterior longitudinal ligaments, thereby providing additional stability to the spinal column during healing or fusion.

In further preferred aspects of the method, the insert is positioned through a percutaneous cannula having an oval, racetrack, or other non-symmetric cross-section. By aligning a major axis of the cross-section of the cannula in an orientation parallel to the intervertebral space between the adjacent vertebrae, the insert may be introduced in the desired orientation with the minor axis of the cross-section of the cannula spanning between the two adjacent vertebrae. Accordingly, in preferred aspects of the invention, the cannula is generally oval or racetrack-shaped in cross-section such that its cross-sectional area is substantially reduced from that of a generally circular cross-sectional cannula, reducing patient trauma and facilitating accurate placement of the insert into the patient's intervertebral space when the cannula is initially received into the patient.

Conveniently, the insert may be manipulated by an insertion tool which is removably attached to the posterior end of the insert. A torque wrench can be used in conjunction with the insertion tool to measure the amount of torque necessary to secure the insert into position. In addition, prior to introduction of the insert, an oval or racetrack shaped coring device can be used to cut a hole in the annulus of the disk as well as to remove osteophytes.

In one preferred aspect, the present insert is removable and is inserted only temporarily such that an increased intervertebral space can be provided allowing temporary increased surgical access therein, such as when performing a discectomy. In an alternative aspect, the insert is designed to be implanted permanently. In both aspects of the invention, the insert is introduced between adjacent vertebrae, preferably with minimal or no prior mechanical distraction, and rotated by about 90 degrees to establish increased intervertebral spacing by camming apart the adjacent vertebrae. If temporary, the insert has smooth flattened vertebral support surfaces so that it may be easily removed. If permanent, the insert has penetrating elements extending from flattened vertebral support surfaces, and the insert is firmly anchored into position by being rotated into position such that the penetrating elements extending therefrom are firmly embedded into the surfaces of the adjacent vertebrae.

In a second method, first and second inserts are positioned laterally spaced-apart from one another between the adjacent vertebrae with the inserts preferably being oriented at an angle to one another. Most preferably, this angle may range from 70° to 135° and is most preferably about 90 degrees. As a result of the angled orientation of the first and second inserts with respect to one another, increased vertebral stability is provided, due to the fact that the inserts will have their rotational axes oriented at an angle to one another. Preferably, the angle between the inserts will be generally perpendicular. An advantage of such increased stability is that the potential for vertebral fusion is increased.

In further aspects of the invention, more than two inserts are positioned in the patient's intervertebral space. In a preferred aspect, inserts are positioned in the patient's intervertebral space in pairs or quartets, however, positioning of a greater number, including an odd number of inserts is also contemplated.

In a preferred aspect of the second method, first and second inserts are received in separate cannulae which are each introduced percutaneously through the patient's back at generally perpendicular angles to one another. Preferably, each cannula has a non-symmetrical cross-section which can include an oval or racetrack-shaped cross-section. In a preferred aspect, the inserts are each introduced posterolaterally at a right angle to one another, similar to a preferred method of inserting a single insert as was described above, with the size and shape of the inserts creating the proper lordotic angle between the adjacent vertebrae.

The posterolateral approach offers the benefit of introducing each insert while avoiding damage to the anterior and posterior longitudinal ligaments, interspinous ligaments and the facet joint capsules, while enabling the positioning of the inserts at generally right angles to one another with each insert being at an angle of about 45° to the sagittal plane of the patient. Since the first and second inserts may each be inserted and anchored into position through respective percutaneous cannulae, a very minimally invasive surgical technique is provided.

The present invention also encompasses various intervertebral inserts which are specifically shaped with outwardly facing convexly curved camming surfaces to cam apart the adjacent vertebrae offering the advantage of reducing the tendency of the adjacent vertebrae to move horizontally with respect to one another. In addition, the present inserts may be tapered from a narrow anterior end to a wide posterior end in their width dimension to facilitate their insertion between adjacent vertebrae. Additionally, the inserts may be formed with vertebral engaging surfaces which are angled with respect to one another to taper from a tall anterior end to a short posterior end in their height dimension such that the inserts preserve a desired lordotic angle between the adjacent vertebrae when inserted therebetween and rotated into an anchored position. (Herein, the width of the insert is defined as the distance separating the two convexly curved outer surfaces and the height of the insert is defined as the distance separating vertebral support surfaces disposed between the two convexly curved outer surfaces).

Each of the various inserts are preferably provided in a range of different sizes, such that an appropriate size of insert can be selected for different intervertebral geometries and tissue conditions to achieve a desired intervertebral separation distance.

Each of these inserts preferably comprises a body having an anterior end, a posterior end, a rotational axis extending between the ends, a pair of outwardly facing convexly curved camming surfaces, and a pair of opposite generally flat vertebral support surfaces.

The outwardly facing convexly curved camming surfaces are adapted to engage, and to separate by camming action, the opposed adjacent vertebrae when the insert is initially placed between the vertebrae and then subsequently rotated. In a preferred aspect of the invention, an outwardly facing convexly curved surface is understood to mean a surface having a degree of curvature corresponding to an arc section defined by an angle in the range of 15 to 40 degrees, and most preferably about 20 degrees.

Each of the opposite outwardly facing convexly curved camming surfaces engages an opposite vertebra, and throughout the camming motion, each of the vertebrae are in contact with an opposite smooth curved outwardly facing convex surface of the implant. An advantage of the present invention is that, by avoiding contact between sharp edges on the insert and the vertebrae as the vertebrae are cammed apart is that minimal damage is done to the surface of the vertebrae. In addition, rotation of the insert pushes apart the adjacent vertebrae without tending to cause the adjacent vertebrae to move side-to-side with respect to one another.

Important advantages of camming apart the adjacent vertebrae using the present convexly curved outer surfaces of the insert are its minimally invasive nature due to the fact that the need for pre-distraction of the vertebrae is substantially reduced or eliminated. Since such distrators do not need to be first introduced in the intervertebral space, chiseling or drilling is not necessary prior to the introduction of the insert. As such, the present insert is ideally suited for reducing post-operative disc space collapse.

At its posterior end, the implant has a preferred height in the range of 4 to 14 mm and a width in the range of 6 to 16 mm. In a preferred embodiment, the posterior end of the insert is dimensioned such that the height of the insert is in the range of 1.5 to 3 times its width. Most preferably, the height of the insert is about 2 times greater than its width.

Preferably, the vertebral support surfaces, (which are disposed between the two convexly curved outer surfaces), are generally flattened to support the adjacent vertebrae thereon and are also angled with respect to one another, (being spaced closer together at the posterior end of the insert and farther apart at the anterior end of the insert), such that a proper lordotic angle is achieved between the adjacent vertebrae when the insert is rotated into position.

For ease of accessing the intervertebral space, especially in a posterolateral approach as will be explained, the width of the leading anterior end of the insert is preferably thinner than the width of the posterior end of the insert.

Selecting the appropriate range for the degree of curvature of the outwardly convex camming surfaces provides a balance between the following two competing needs. Should the degree of curvature be too small, the insert will assume a more flattened shape. Camming with such a flattened insert will be very difficult, requiring excessive force to pry apart the adjacent vertebrae. On the other hand, should the degree of curvature instead be too large, the insert will assume a more rounded shape, such that the vertebrae can only be cammed apart a short separation distance when the insert is rotated 90°. This is due to the fact that the maximum distance the vertebrae can be cammed apart will be equal to the difference between the lengths of the major and minor cross sectional axes of the insert. For a more rounded insert, the major and minor axes of the insert will tend to be close to the same distance, such that camming will not substantially separate the vertebrae.

In addition, should the degree of curvature be too large, the insert will assume a more rounded shape, necessitating a larger insert which is much more difficult to introduce between the adjacent vertebrae, requiring additional vertebral pre-distraction. A large rounded insert also has the additional disadvantage that much greater tissue displacement would occur as the insert is introduced into the intervertebral space through a large rounded cannula.

Preferably, the opposite flat vertebral support surfaces disposed between the outwardly facing convexly curved surfaces are preferably disposed at an angle to a central longitudinally extending rotational axis of the insert. Selection of the appropriate range of size for the width of these opposite flat surfaces provides a balance between the following two competing needs. Should the flat surfaces be too narrow, the insert will have an insufficiently load bearing surface and could be less stable and tend to tip over after it has been rotated into position. On the other hand, should the opposite flat surfaces be too wide, the size of the implant will be undesirably increased, giving it a more rectangular shape and making it more difficult to introduce into the intervertebral space in a minimally invasive procedure.

In a preferred aspect of the invention, a cannula having a non-symmetric cross-section may be used for percutaneously introducing the insert with a minimal amount of tissue disruption. The non-symmetric cross-section can include an oval-shaped cannula having a lumen shaped to slidingly mate with the opposite outwardly facing convexly curved camming surfaces of the insert, thereby preventing the insert from rotating while in the cannula. The use of such an oval-shaped cannula permits the insert to be introduced percutaneously with minimal invasion and surrounding tissue damage as compared to a larger volume round cannula. Moreover, the flattened and elongated cross-sectional shape of an oval-shaped cannula permits it to easily position the insert in a desired orientation between the adjacent vertebrae.

In a preferred aspect, the insert has opposite, flattened vertebral support surfaces which taper inwardly towards the rotational axis at the anterior end of the insert. Additionally, when the insert is introduced at an angle to the sagittal plane, (such as when inserting left and right inserts disposed at an angle to one another), the vertebral support surfaces on these inserts can also be angled with respect to one another from side to size across the insert. This tapering and angling permits the insert to provide the required lordosis angle along the anterior-posterior contour of the opposite adjacent vertebrae.

Should it be desired that the insert be implanted permanently between the adjacent vertebrae, the insert preferably includes anchoring fins or barbs which extend from the opposite flat surfaces. The anchoring fins may be spaced apart in an anterior-posterior direction. Rotation of the insert causes the anchoring fins to penetrate and lock firmly into the adjacent vertebral surfaces. The anchoring fins may have apical, (i.e., saw tooth), textured surfaces to increase their ability to penetrate the vertebral endplates and expanded cross-sectional bases to increase their ability to remain firmly anchored. Moreover, the anchoring fins may be barbed so as to increase their ability to remain firmly secured into the adjacent vertebral surfaces. In a preferred aspect, the sides of the fins display an outwardly convexly curved shape, assisting in vertebral camming.

Fenestrations which pass through the insert may also be provided so as to receive bone graft therein and promote bone growth therethrough, thus firmly holding the insert in position over time.

The insert may be fabricated from any bio-compatible material which is strong enough to support the spinal load passing therethrough. For example, the insert may be fabricated from stainless steel, titanium or carbon fiber composites. Such materials can be used whether the insert is to be implanted only temporarily, (such as during a discectomy), or permanently.

In another aspect of the invention, the insert is fabricated from donor bone graft material which may comprise human, autologous, allographic, xenographic, or other osteoinductive and osteoproliferative bone graft material.

In another aspect of the present invention, the insert is fabricated from a bio-absorbable material such that it will eventually be absorbed into the patient's body over time. For example, in a preferred aspect, the material used would be poly-L-lactic acid, polyglycolic acid, collagen, calcium phosphates, bio-absorbable ceramics, or any combination thereof which imparts sufficient initial implant strength to distract the vertebral bodies, to maintain a preferred vertebral spacing for a period of time, and which would be resorbed thereafter to promote natural disc healing. By varying the composition of the bio-absorbable material, the speed of bio-absorption can be adjusted per the desired use of the insert.

For example, should the insert be bio-absorbed over a short term such as 6 to 12 months, the insert will tend to promote disc re-generation by allowing the regenerated disc tissues to support progressively more of the spinal load as the disc tissues heal and the insert is absorbed. Conversely, should the insert be bio-absorbed slowly over a long term such as 2 to 3 years, the insert will instead tend to promote fusion by minimizing or eliminating normal motion for an extended period of time.

In another aspect of the present invention, an orthopedic insert having an electronic transducer is provided. The insert has a body which is adapted to be implanted within or adjacent to a bone of a patient, wherein the insert has at least one surface which will be loaded by bone motion pressing against the implant. The transducer within the insert body is mechanically coupled to the surface of the bone, or alternatively, is received into bone graft material, and produces electrical current of a type and in an amount sufficient to induce osteogenesis in the intervertebral space and in the bone or bone graft material in particular. In a preferred aspect, the insert comprises an embedded or jacketed piezoelectric crystal or crystals acting as a mechanical-electrical transducer.

BRIEF DESCRIPTION OF THE DRAWINGS

FIG. 1A is a perspective view of a permanently-implantable insert of the present invention;

FIG. 2 is a side sectional elevation view of the insert of FIG. 1A;

DEFINITIONS

Figure 1B:
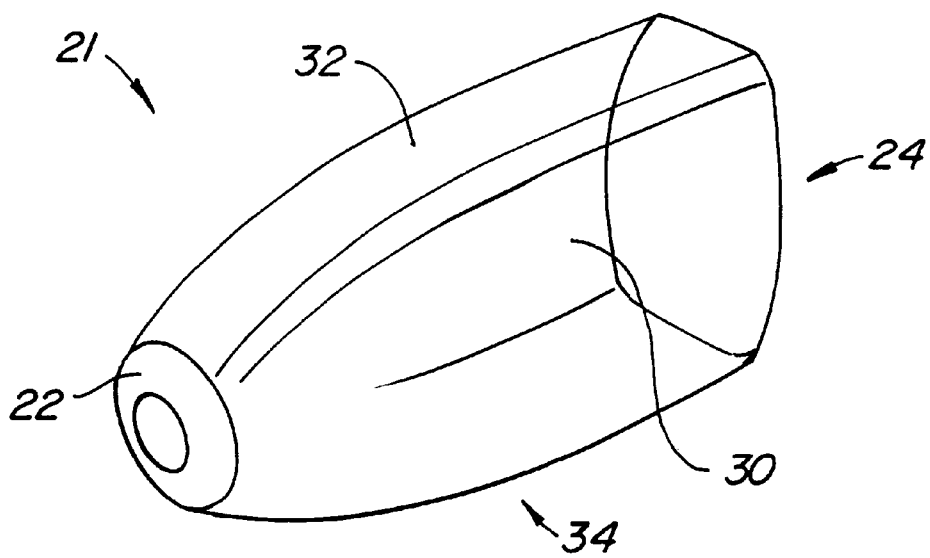
FIG. 1B is a perspective view of a temporarily-implantable insert of the present invention.
Figure 3:
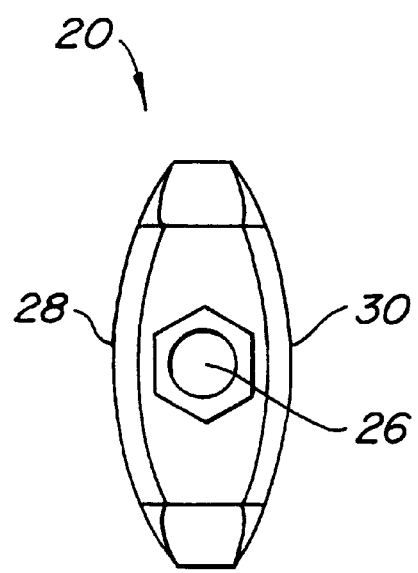
FIG. 3 is a front elevation view of the insert of FIG. 1A.

As used herein, the following terms are understood to have the following meanings:

"camming"—increasing intervertebral separation by rotating opposite convexly curved sides of an intervertebral insert against adjacent vertebrae.

"distraction"—pulling apart, separating, or increasing the distance between adjacent opposite vertebrae by physical or mechanical means.

"fusion"—complete ingrowth of bone tissue between adjacent vertebrae.

"outwardly facing convexly curved camming surface"—a surface having a degree of curvature corresponding to an arc section defined by an angle in the range of 15 to 40 degrees, and most preferably about 20 degrees.

"posterolateral"—behind and to one side.

"racetrack-shaped"—a shape having two elongated parallel sides and two curved ends.

DESCRIPTION OF THE SPECIFIC EMBODIMENTS

The present invention comprises intervertebral inserts, methods and kits for separating and stabilizing adjacent vertebrae by camming apart the adjacent vertebrae with novel shaped intervertebral inserts having outwardly facing convexly curved camming surfaces disposed opposite one another. Both permanent and temporary intervertebral inserts are provided.

A first embodiment of a permanent intervertebral insert 20 is best seen in FIGS. 1A, 2, 3, 4A and 5. Insert 20 has a posterior end 24 and an anterior end 22. A longitudinally extending central rotational axis 26 extends between ends 22 and 24. To provide optimal intervertebral support, the length of insert 20 (i.e., the separation distance between ends 22 and 24) is in the range of 15 to 30 mm, and is most preferably about 25 mm.

Figure 4A:
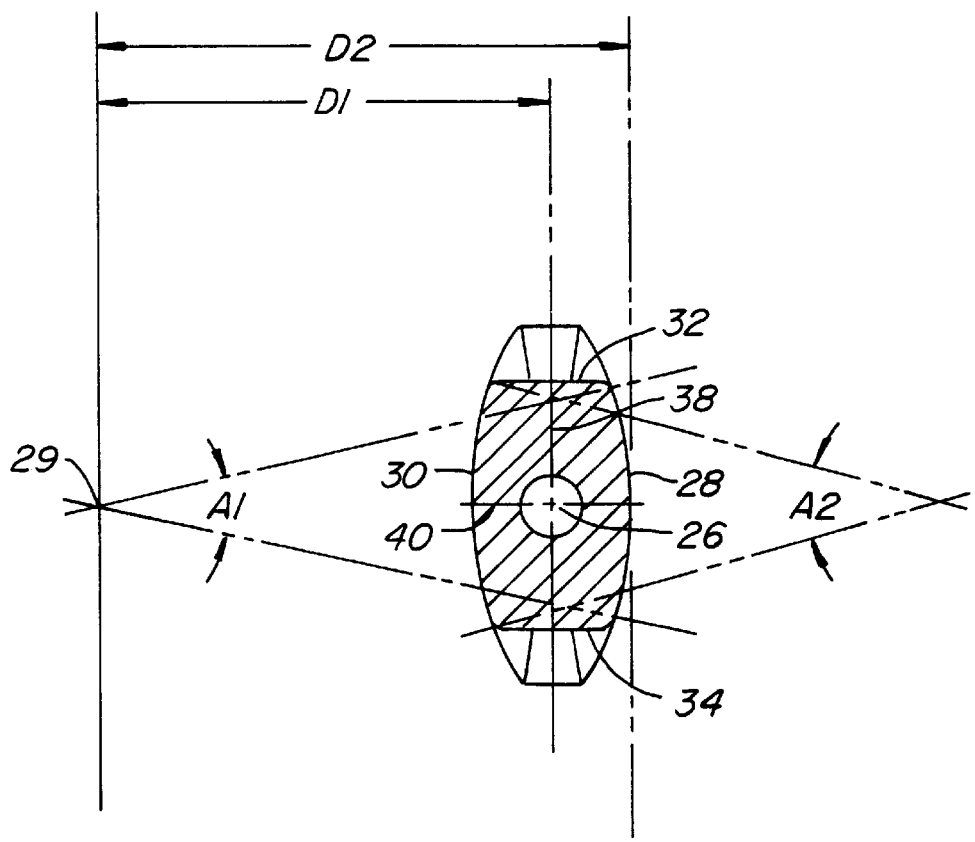
FIG. 4A is a rear elevation view of the insert of FIG. 1A.

A pair of outwardly facing convexly curved camming surfaces 28 and 30 are disposed on opposite sides of insert 20 at an angle to axis 26 as shown. Surfaces 28 and 30 are adapted to engage, and to separate by camming action, the opposed vertebral surfaces when insert 20 is placed between adjacent vertebrae and rotated into an anchored position, as will be described. In a preferred aspect, outwardly facing convexly curved camming surfaces 28 and 30 are selected to have a degree of curvature which facilitates camming with the degree of being neither too large (producing a more rounded insert which can only cam the vertebrae apart a short distance), nor too small (producing a flatter insert which requires greater force to cam into position). As shown in FIG. 4A, an appropriate degree of curvature of outwardly facing convex surfaces 28 and 30 occurs when they are dimensioned to represent an arc segment defined by identical angles A1 and A2 which are in the range of 15 to 40 degrees, and is most preferably about 20 degrees.

Selection of the optimal range for the dimension of angles A1, A2, A3 and A4 ensures that the degree of curvature shown in outwardly facing convex surfaces 28 and 30 is neither too small nor too large. Should the amount of curvature be too small, insert 20 will assume a more flattened shape, allowing easy intervertebral access, but impeding camming action. Should the amount of curvature instead be too large, insert 20 will assume a more rounded shape, becoming much more difficult to introduce between the adjacent vertebrae without requiring vertebral pre-distraction. Moreover, a large rounded insert has the additional disadvantage that much greater tissue displacement would occur as the insert is introduced into the intervertebral space. Preferably, outwardly facing convex surfaces 28 and 30 will each be dimensioned to be of a size ranging from 6 to 16 mm between opposite flattened surfaces 32 and 34, depending upon the size of the insert.

Figure 4B:
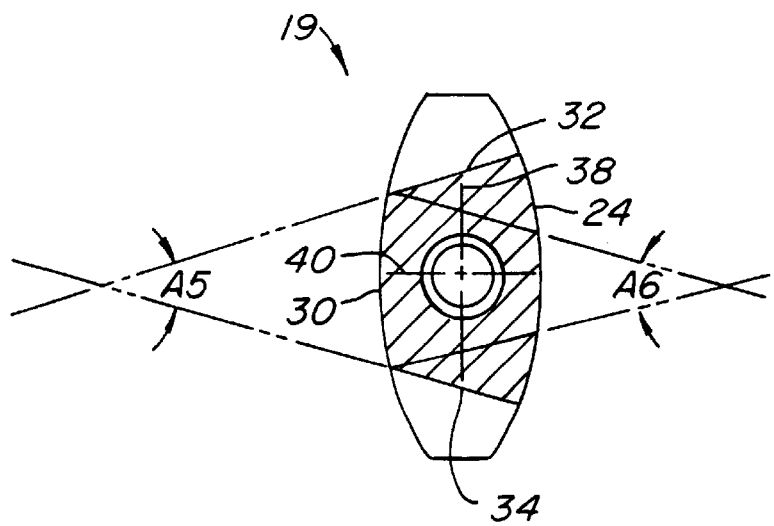
FIG. 4B is a rear sectional elevation view of an insert similar to that of FIG. 1A, but instead having its opposite vertebral supporting surfaces disposed at an angle to one another.

In an alternate non-symmetrical embodiment shown in FIG. 4B, implant 19 has surfaces 32 and 34 which are angled to one another such that outwardly facing convex surface 28 is dimensioned to represent an arc segment defined by an angle A5 which is in the range of 15 to 40 degrees, and is most preferably about 20 degrees. Outwardly facing convex surface 30 is somewhat smaller representing an arc segment defined by an angle A6. The angling of surfaces 32a and 34a with respect to one another as shown in FIG. 4B assists in providing proper lordosis between the adjacent vertebrae when two inserts are positioned at right angles to one another in the intervertebral space, as will be described herein.

As can be seen in both FIGS. 4A and 4B, opposite flattened vertebral support surfaces 32 and 34 are disposed between outwardly facing convex surfaces 28 and 30. As will be explained in conjunction with a preferred method described herein, opposite flattened surfaces 32 and 34 are adapted to provide a flush contact against and thereby buttress adjacent separated vertebrae after insert 20 has been rotated into position. Selection of the optimal dimensions for opposite flattened surfaces 32 and 34 ensures that these surfaces are nether too wide nor too narrow. Should surfaces 32 and 34 be too wide, the size of the insert will be undesirably increased, making it more difficult to introduce into the intervertebral space. On the other hand, should surfaces 32 and 34 be too narrow, the insert will provide insufficient load bearing surface and could be less stable and tend to tip over after it has been rotated into position. Preferably, opposite flattened surfaces 32 and 34 are preferably dimensioned to be in the range of 4 to 12 mm between outwardly facing convex surfaces 28 and 30, depending upon the size of the insert.

Preferably, insert 20 tapers from narrow anterior end 22 to wide posterior end 24 to facilitate introduction of the implant into the intervertebral space when the insert is introduced posterolaterally into the patient, as will be described.

Tapering of insert 20 facilitates intervertebral insertion and is provided by outwardly facing convex surfaces 28 and 30 being disposed at an angle to axis 26. The degree of tapering between posterior end 24 and anterior end 22 also assists in permitting the adjacent vertebrae to provide the required lordosis angle when the insert is received therebetween. In the embodiment of FIG. 4B, the angling of surfaces 32 and 34 with respect to one another provides the required lordosis angle when the insert is positioned at an angle to the sagittal plane.

Figure 5:
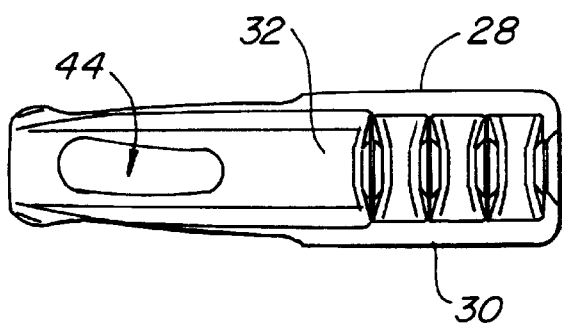
FIG. 5 is a top plan view of the insert of FIG. 1.

As is seen in FIG. 1A, anchoring fins 36 extend outwardly from each of opposite flattened surfaces 32 and 34, and are preferably spaced apart in an anterior-posterior direction parallel to axis 26. Fins 36 may be textured on their projecting edges and expanded at their bases, (as shown in FIGS. 1A and 5), so as to increase their ability to penetrate the vertebral endplates and enhance vertebral stability. Optionally, fins 36 may be barbed so as to increase their ability to remain firmly secured into the opposite adjacent vertebral surfaces.

As is best seen in FIGS. 4A and 4B, insert 20 and insert 19 have a cross-sectional shape which is defined by a long axis 38 and a short axis 40. Axes 38 and 40 are perpendicular to one another and are also both perpendicular to rotational axis 26. Long axis 38 corresponds to the width of the insert and short axis 40 corresponds to the height of the insert. Preferably, the height of the insert is in the range of 1.5 to 3 times the width of the insert. Most preferably, the width of the insert is two times greater than its height. Having a relatively large height as compared to its smaller width, the insert is ideally dimensioned to be inserted between adjacent vertebrae on its side, (preferably percutaneously through an oval-shaped cannula passage, and with minimal or no prior vertebral distraction by dedicated instrumentation), and then rotated into an anchored position therebetween, camming apart the adjacent vertebrae, as will be explained in conjunction with a preferred method.

In addition, for improved camming action, insert 20 has preferred height to width dimensions, with the height being in the range of 1.5 to 3 times greater than said width of the insert. In an preferred aspect, distance D1 in FIG. 4A between vertex 29 of angle A1 and rotational axis 26 is preferably about 85% of the distance D2 between vertex 29 and outer surface 28.

As is best seen in FIGS. 1A, 1B, and 2, inserts 20 and 19 have fenestrations 42 and 44 passing therethrough, with fenestration 42 passing generally perpendicular to outwardly facing convex surfaces 28 and 30 and fenestration 44 passing generally parallel to outwardly facing convex surfaces 28 and 30. Fenestrations 42 and 44 are adapted to receive bone graft material therein and thereby permit an opportunity for bone growth therethrough. Such bone growth therethrough assists in firmly holding the insert in an anchored position. Specifically, fenestration 44 permits bone growth therethrough in a vertical direction along the spinal axis and fenestration 42 permits bone growth therethrough in a direction perpendicular to the spinal axis when the insert is anchored into position between adjacent vertebral discs with its flattened surfaces 32 and 34 providing buttressing support against the vertebrae.

Inserts 20 and 19 can be made of any bio-compatible sterilizable material, including stainless steel, titanium, or carbon fiber composites. In one aspect of the present invention, however, the insert is fabricated from a bio-absorbable material such that it will be absorbed into the patient's body. Suitable bio-absorbable materials include poly-L-lactic acid, polyglycolic acid and calcium triphosphates. A bioabsorbable insert has the advantage that over time it will be absorbed by the body, such that the surrounding spinal and discal tissue will first have an opportunity to heal when the insert is fully supporting the spinal load through the adjacent vertebrae and maintaining the intervertebral disc spacing. Over time, as the insert is absorbed, a steadily increasing portion of the spinal load will be borne by the regenerated discal tissue and a steadily decreasing load will be borne by the insert itself.

Should the insert be bio-absorbed quickly over a short term, (such as 6 to 12 months), the insert will promote disc re-generation by allowing the regenerated disc tissues to support progressively more of the spinal load as the disc tissues heal. Conversely, should the insert be bio-absorbed slowly over a long term, (such as 2 to 3 years), the insert will promote fusion by minimizing or eliminating normal motion for an extended period of time. Specifically, fusion will be promoted by the use of bone graft material and either a 2 to 3 year insert or a permanent insert.

By varying the composition of the bio-absorbable material, the speed of bio-absorption can be optimized per the desired use of the insert. Specifically, the use of collagen or polyglycolic acid will result in an insert which will be bio-absorbed in 6 to 12 months. Alternately, the use of poly-L-lactic acid will result in an insert which will be bio-absorbed in 2 to 3 years.

In another aspect of the present invention, as seen in FIG. 1B, a temporary placement insert 21 is provided. Being removable, insert 21 is ideally suited for intra-operative insertion between adjacent vertebrae to provide working space, thereby temporarily increasing intervertebral spacing, such as when performing surgical procedures including a discectomy.

Insert 21 differs from inserts 20 and 19 in that anchoring fins 36 and fenestrations 42 and 44 (seen on inserts 20 and 19) are not seen on insert 21. Lacking anchoring fins, the insert is more easily removable as it would not firmly anchor itself into the adjacent vertebrae. Moreover, fenestrations 42 and 44 are not required as no bone graft material need be introduced into a temporary implant, which is ideally removed at the end of a surgical procedure. Insert 21 preferably has a length (i.e., a separation distance between ends 22 and 24) in the range of 7 to 25 mm and most preferably 12 mm. Accordingly, insert is somewhat shorter than inserts 20 and 19. As compared to inserts 20 and 19, therefore, insert 21 will provide increased access for other tools to be received in the intervertebral space during procedures such as a discectomy. Fabrication of such a temporary-insertion insert can be from a variety of sterilizable bio-compatible materials including stainless steel which has the advantage of reusability.

Figure 8:
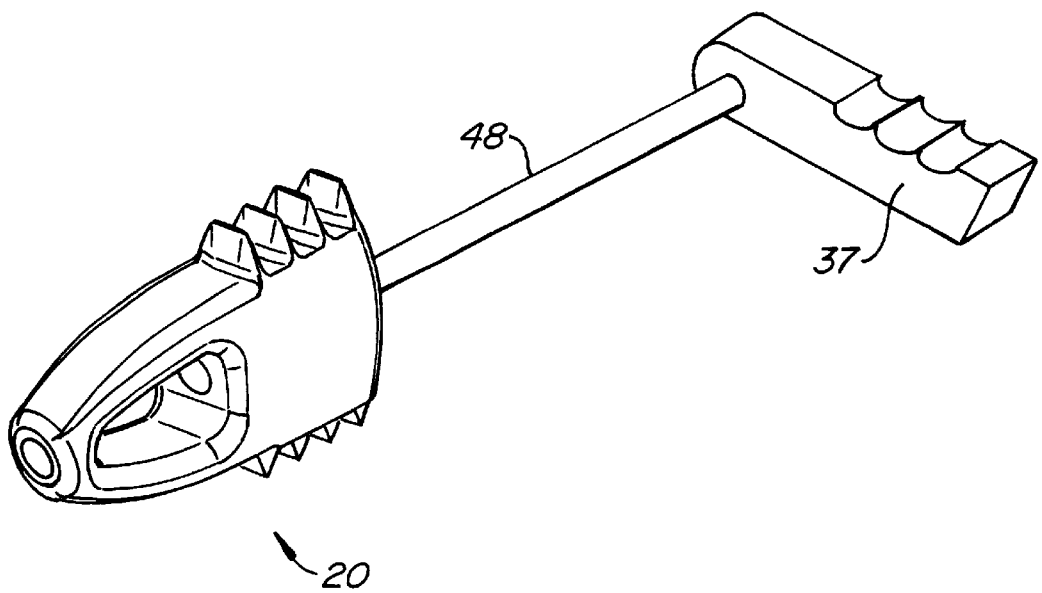
FIG. 8 is a perspective view of the insert of FIG. 1 as connected to a positioning rod.

When using either insert 20 or 19 or 21, an elongated positioning rod 48 is preferably received into bore 25 in posterior surface 24 of insert 20, as seen in FIG. 8 as used with insert 20. Bore 25 may be non-cylindrical or other shape such as hex-shaped to securely interlock with a non-symmetrical, hex-shaped, or keyed end 49 of rod 48. Rotation of rod 48 causes insert 20 to rotate about axis 26, thereby causing outwardly facing camming surfaces 28 and 30 to engage, separate and stabilize adjacent vertebrae. Preferably, rod 48 is releasably secured to insert 20 by a ball detente mechanism such that insert 20 can conveniently be left in an anchored position between the adjacent vertebrae while rod 48 is detached and then removed.

A torque wrench 37 can be applied to rod 48 such hat the amount of torque necessary to cam apart the adjacent vertebral surfaces 50 and 52 can be measured. Such measurement can be used to determine the most appropriate size of insert to be used for any particular intervertebral application, as will be described in a preferred method herein.

In a preferred aspect, rod 48 and torque wrench 37 can be combined into a single unit for ease of manipulation. Torque wrench 37 permits measurement of the torque necessary to rotate the insert into position. However, torque wrench 37 may also include a lockout mechanism for shutting off the torque measurement capability of the wrench and eliminating play in the wrench, thereby permitting back and forth rotation of the insert within a narrow range of movement corresponding to a narrow range of movement of the torque wrench, (for example, plus or minus 15 degrees), such that the insert can be rocked back and forth into a firmly anchored position. Such a lockout mechanism will preferably be engaged after the insert is first introduced and then rotated by 90 degrees to engage anchoring fins 36 into vertebrae 50 and 52. Accordingly, the locking mechanism permits the insert to be easily rocked back and forth, causing fins 36 to be worked into an anchored position in vertebrae 50 and 52 while the torque wrench and rod can be moved through a greater arc of motion.

Figure 9B:
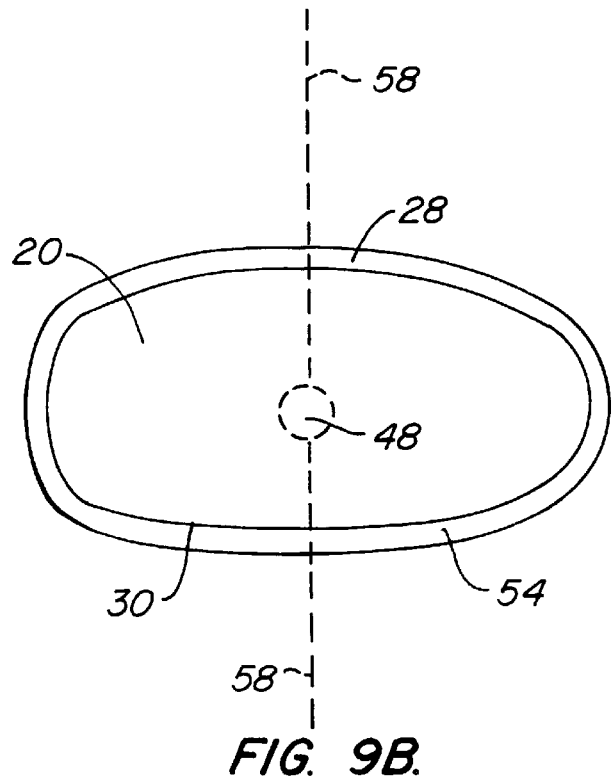
FIG. 9B is a end view taken along line 9B—9B in FIG. 9A.
Figure 9A:
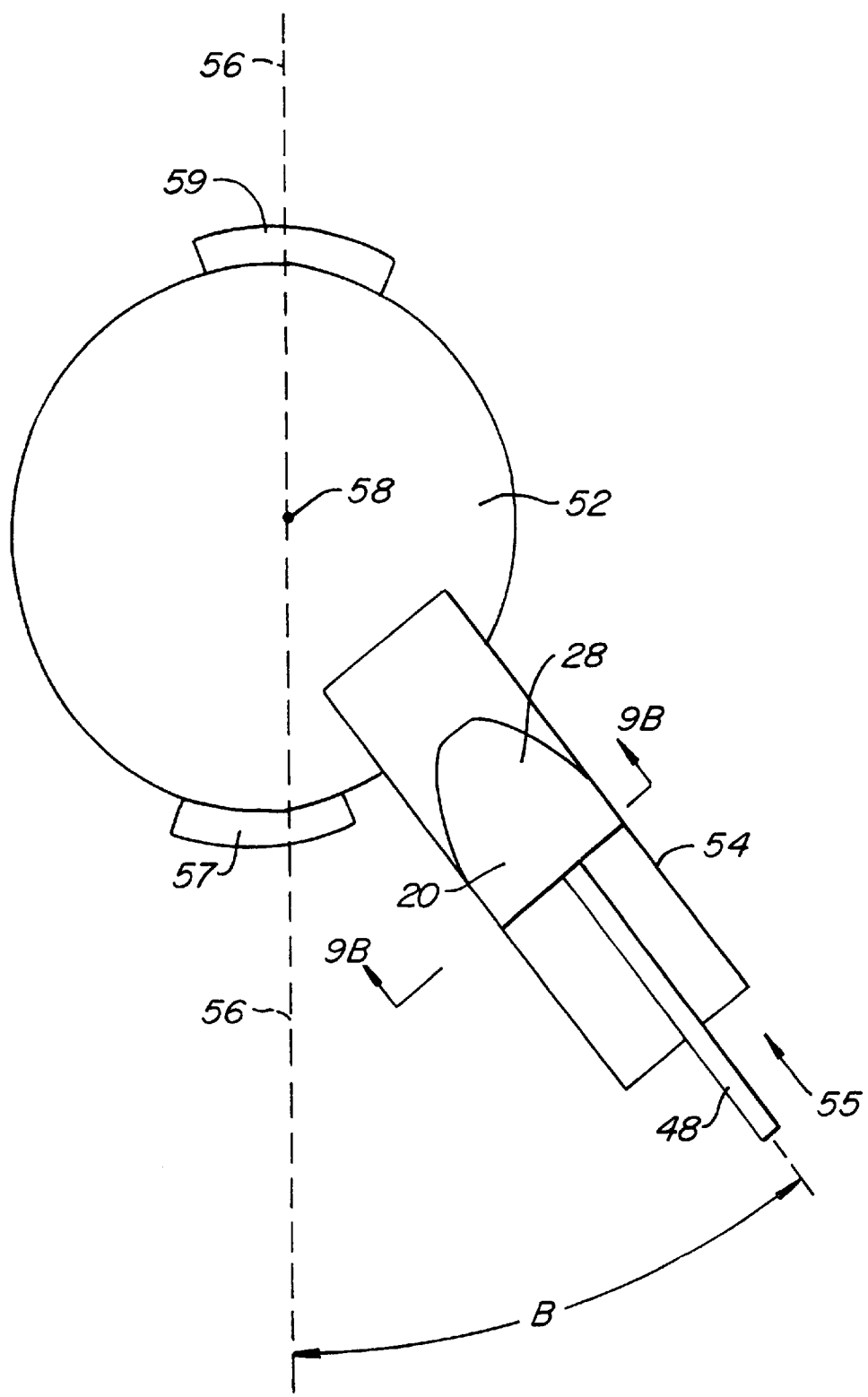
FIG. 9A is a top plan view of the insert of FIG. 1 as received in an oval shaped cannula.

Inserts 20, 19 and 21 are ideally adapted for delivery through a cannula having a non-symmetric cross-section which may be used for percutaneously introducing the insert with a minimal amount of tissue disruption. As is shown in FIGS. 9A and 9B, (which illustrates insert 20 as an example), the non-symmetric cannula can include an oval-shaped or racetrack-shaped cannula 54 having a lumen 55 shaped to slidingly mate with opposite outwardly facing convex camming surfaces 28 and 30 of insert 20, thereby preventing insert 20 from rotating while in cannula 54. The use of cannula 54 permits insert 20 to be introduced percutaneously with minimal invasion and surrounding tissue damage as its flattened elongated cross-sectional shape permits it to be easily received between the adjacent vertebrae 50 and 52.

Figure 6:
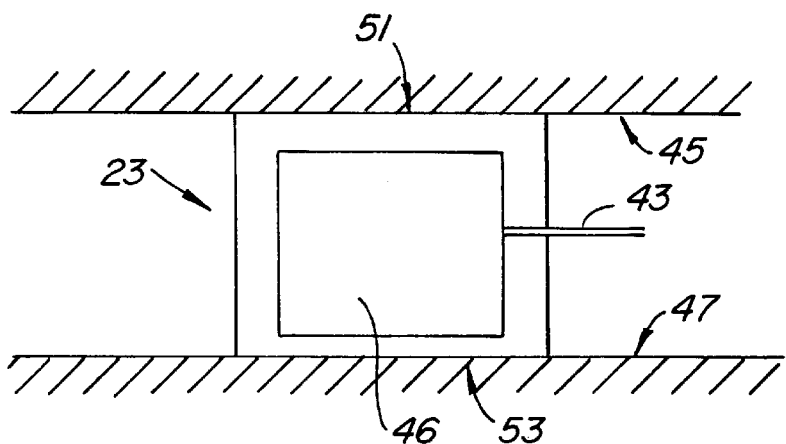
FIG. 6 is a schematic sectional side elevation view of an implant having an electronic transducer therein.

In another aspect of the present invention, as shown schematically in FIG. 6, an orthopedic insert 23 having an electronic transducer 46 is provided. Insert 23 can comprise any suitable insert and is not limited solely to intervertebral inserts and is also not limited to those intervertebral inserts corresponding to the above described geometries of inserts 20, 19 and 21. Insert 32 has a body which is adapted to be implanted within or adjacent to bone 45 of a patient, wherein the insert has at least one surface 51 which will be loaded by bone motion against the implant. As shown in FIG. 6, insert 23 may simultaneously be placed adjacent to bones 45 and 47 with surfaces 51 and 53 being loaded by bone motion. In one preferred aspect of the present orthopedic insert, bones 51 and 53 are adjacent vertebrae and loading of transducer 46 will be provided by normal spinal loading. In another aspect, insert 32 can be configured as a dental prosthesis. Insert 32 is not limited in its application to positioning at any particular location in the body. Rather, all that is required is a periodic motion which tends to compress and/or stretch apart surfaces 51 and 53 of the insert. Repetitive cycling of loading on insert 32 operates to produce an electric current which, through wiring, can be directed to preferred locations in the body to promote bone growth.

In alternative aspects of the invention, transducer 46 may be embedded in various orthopedic or endodontic appliances such as bone and joint prostheses, plates, intermedullary rods, screws, external fixators, or any other appliances in which mechanical energy can be channeled to bone or peri-osseus tissue to stimulate bone formation and/or reduce bone loss.

Transducer 46 operates to generate an electric current when insert 23 is subjected to stress loading. Transducer 46 can comprise a piezoelectric crystal which generates an electric current when insert 23 is subjected to normal repetitive loading through the patient's spine.

Alternatively, transducer 46 can comprise a battery which continuously generates an electric current. A wire 43 operates to deliver the generated current to a preferred bone, bone graft or other area for bone formation. The body of insert 23 may itself act as a ground for wire 43. Transducer 46 may be mechanically coupled to the surface of either or both of bones 51 or 53, such as by anchoring fins, screws or bone cement. Transducer 46 operates to produce electrical voltage and current of a type and in an amount sufficient to induce osteogenesis in the bone.

Specifically, a preferred current is in the range of 1 to 10 microamps, and most preferably about 2.5 microamps/cm$^2$.

Figure 7:
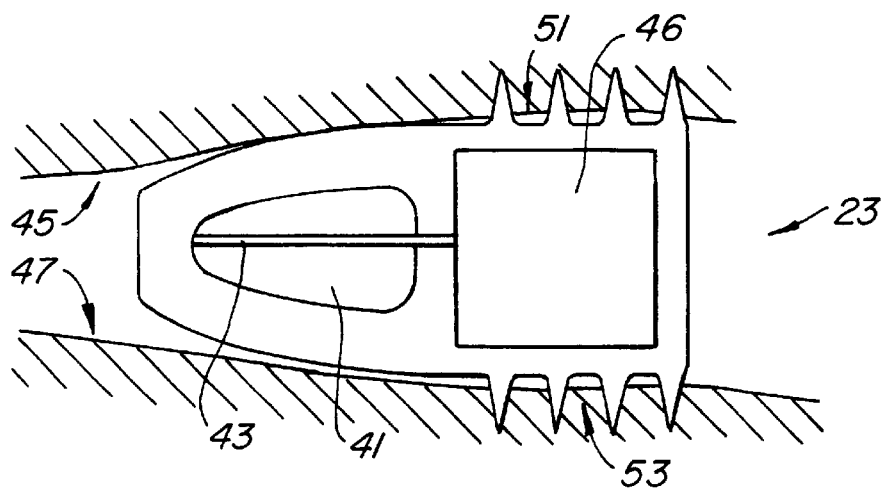
FIG. 7 is a sectional side elevation view of a permanently-implantable insert with an electronic transducer therein.

FIG. 7 illustrates one particular embodiment of an intervertebral application of orthopedic insert 23. Specifically, insert 23 is implanted between adjacent vertebrae 45 and 47. Bone graft material is then introduced into space around the insert as well as within fenestration 41 such that wire 43, (passing across fenestration 41), will apply current directly to the bone graft material, thereby promoting osteogenesis when vertebrae 45 and 47 repeatedly load surfaces 51 and 53 of insert 23.

Figure 11:
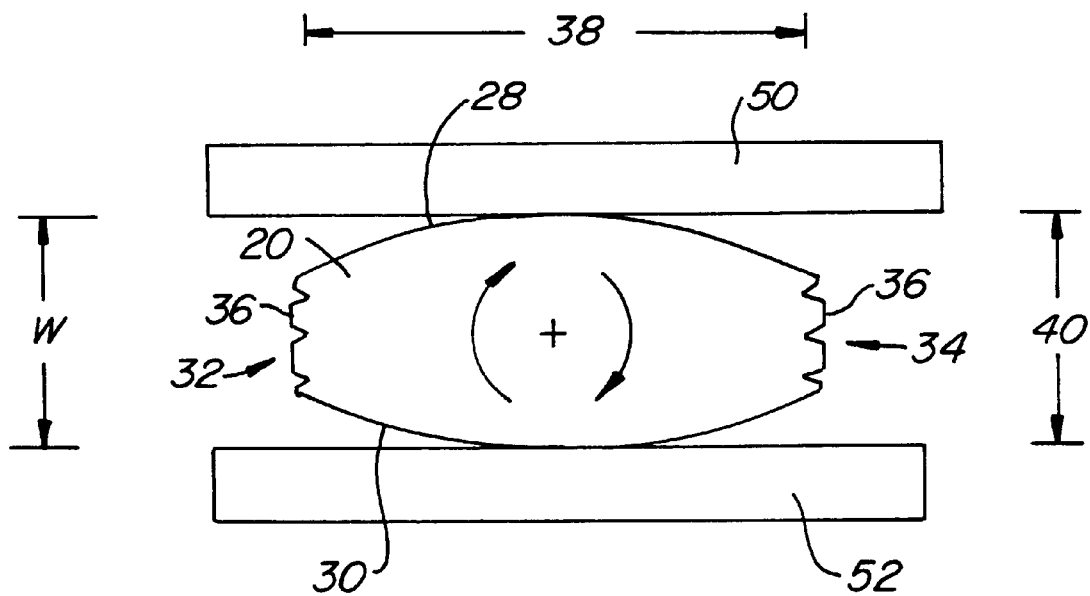
FIG. 11 is a perspective view of an insert as received between adjacent vertebrae.
Figure 12:
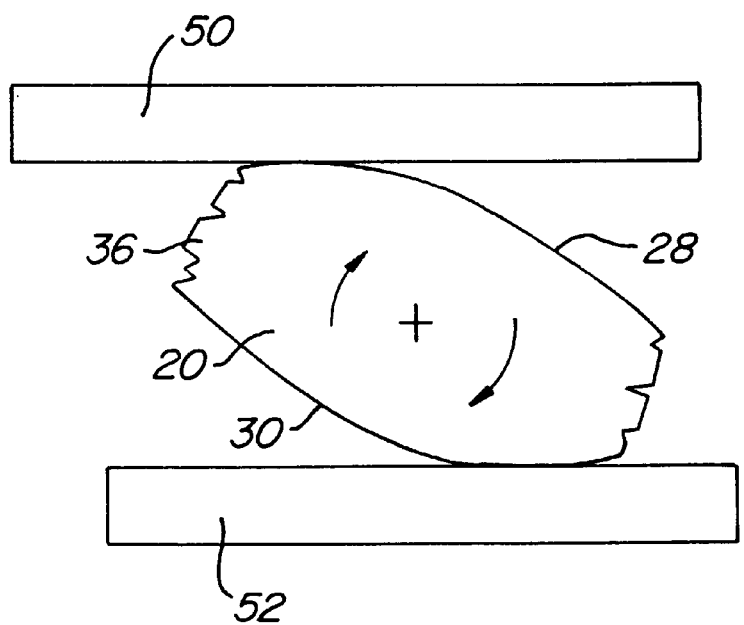
FIG. 12 is a perspective view illustrating camming action as the insert of FIGS. 9A and 9B is rotated.
Figure 13:
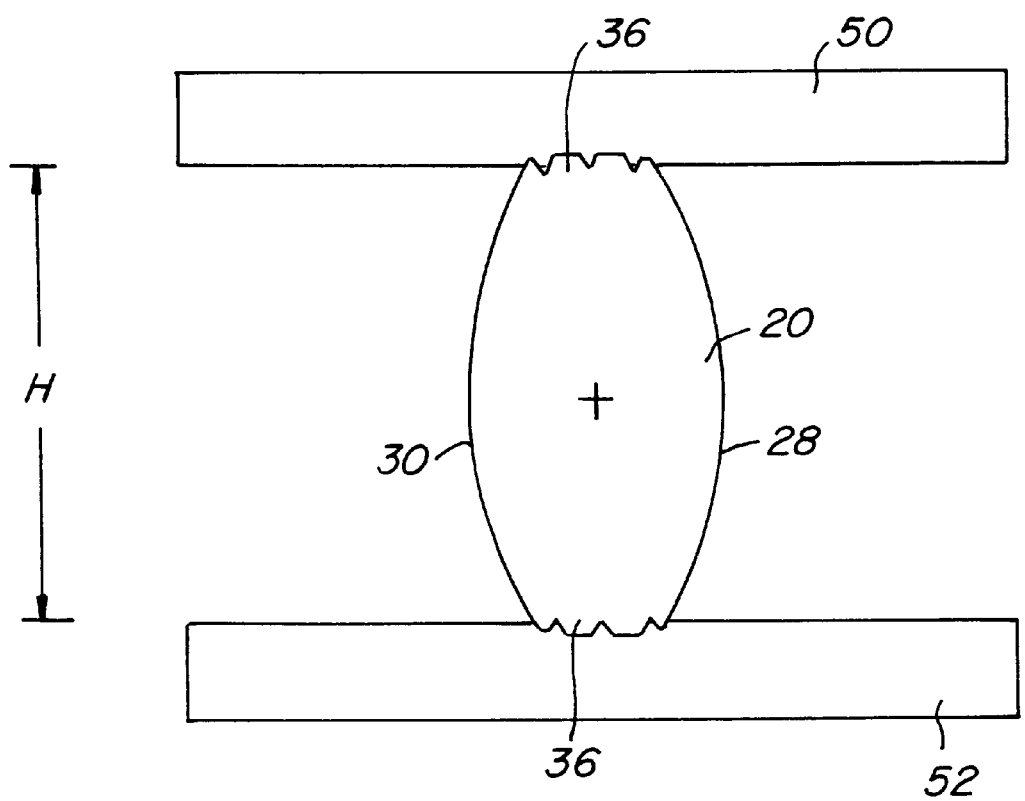
FIG. 13 shows the insert of FIG. 11 in a fully rotated position, buttressing against adjacent vertebrae.

The present inserts 20, 19, 21 and 32 are particularly well suited for use in methods of separating and stabilizing adjacent vertebrae by positioning an insert therebetween. FIGS. 11, 12 and 13 illustrate a preferred method as carried out in conjunction with permanent insert 20. This preferred method can also be carried out (with minor variations which will be explained) in conjunction with temporary insert 21.

The preferred method is appreciated by sequentially viewing FIGS. 11, 12 and 13. In this method, adjacent vertebrae 50 and 52 are separated and stabilized by introducing insert 20 therebetween (in the orientation as seen in FIG. 11), rotating insert 20 to engage outwardly facing convex surfaces 28 and 30 against vertebrae 50 and 52, respectively (as seen in FIG. 12), and anchoring insert 20 between adjacent vertebrae 50 and 52 (as seen in FIG. 13). As seen in FIG. 11, insert 20 is preferably inserted between vertebrae 50 and 52 with its short axis 40 being generally perpendicular to vertebrae 50 and 52 and its long axis 38 being generally parallel to vertebrae 50 and 52. Having a small height in relation to its width, insert 20 can easily be inserted between the adjacent vertebrae with minimal or no prior distraction of the vertebrae, which would require highly invasive distractor tools being first inserted.

In addition, the angling of surfaces 28 and 30 to axis 26 results in a tapered shape of the insert from a narrow anterior end 22 to a wide posterior end 24, which facilitates vertebral distraction when the insert is first introduced between the vertebrae, even prior to its rotation. Specifically, when insert 20 is introduced into the vertebral space in a posterior approach, narrow anterior end 22 is introduced first, operating as a wedge to separate the adjacent vertebrae, as the insert is received therebetween.

When rotating insert 20 into position, curved surfaces 28 and 30 operate to smoothly cam apart vertebrae 50 and 52 (as seen in FIG. 12), and flattened vertebral support surfaces 32 and 34 become flush with the surfaces of vertebrae 50 and 52, (as seen in FIG. 13), thereby providing a stable buttressing support between the adjacent vertebrae, as anchoring fins 36 protrude therein. In the case of permanently-implanted insert 20, the anchoring of insert 20 is preferably accomplished by rotating the insert by approximately 90 degrees such that its anchoring fins 36 become embedded in the surface of vertebrae 50 and 52, thereby holding insert 20 firmly in position. During anchoring, fins 36 may be rotated back and forth by a small amount, such as 10 to 15 degrees, to cause fins 36 to firmly dig into the surfaces of the opposite vertebrae. In the case of insert 21 which is temporarily-implanted during a surgical procedure, anchoring fins are not provided and therefore insert 21 is not anchored into position. Therefore, insert 21 can easily be removed by being rotated again by 90 degrees to be removed. Such subsequent rotation can either be in the same direction as shown in FIGS. 11 to 13, or in the opposite direction. An advantage of rotating insert 21 in a direction opposite to that shown in FIG. 12 to remove the insert is that insertion and removal of the insert will not tend to cause lateral movement of one vertebrae with respect to the other. Temporary removable insert 21 can thus be employed to jack apart vertebrae 50 and 52 such that the intervertebral space can be increased during surgical procedures such as a discectomy.

Figure 17:
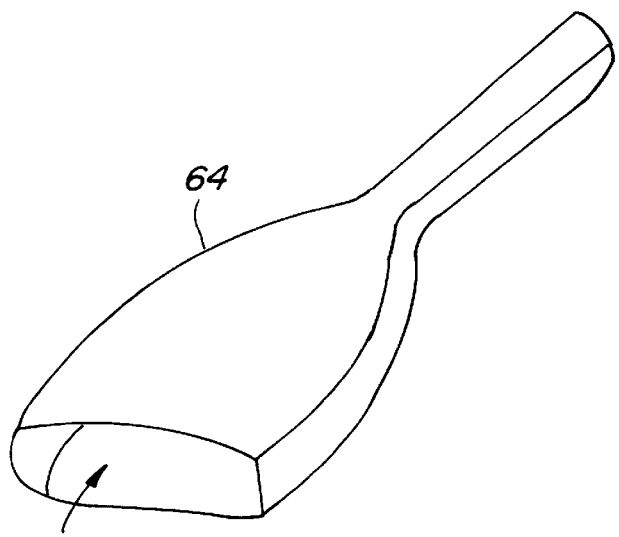
FIG. 17 is a perspective view of an oval coring device.
Figure 18:
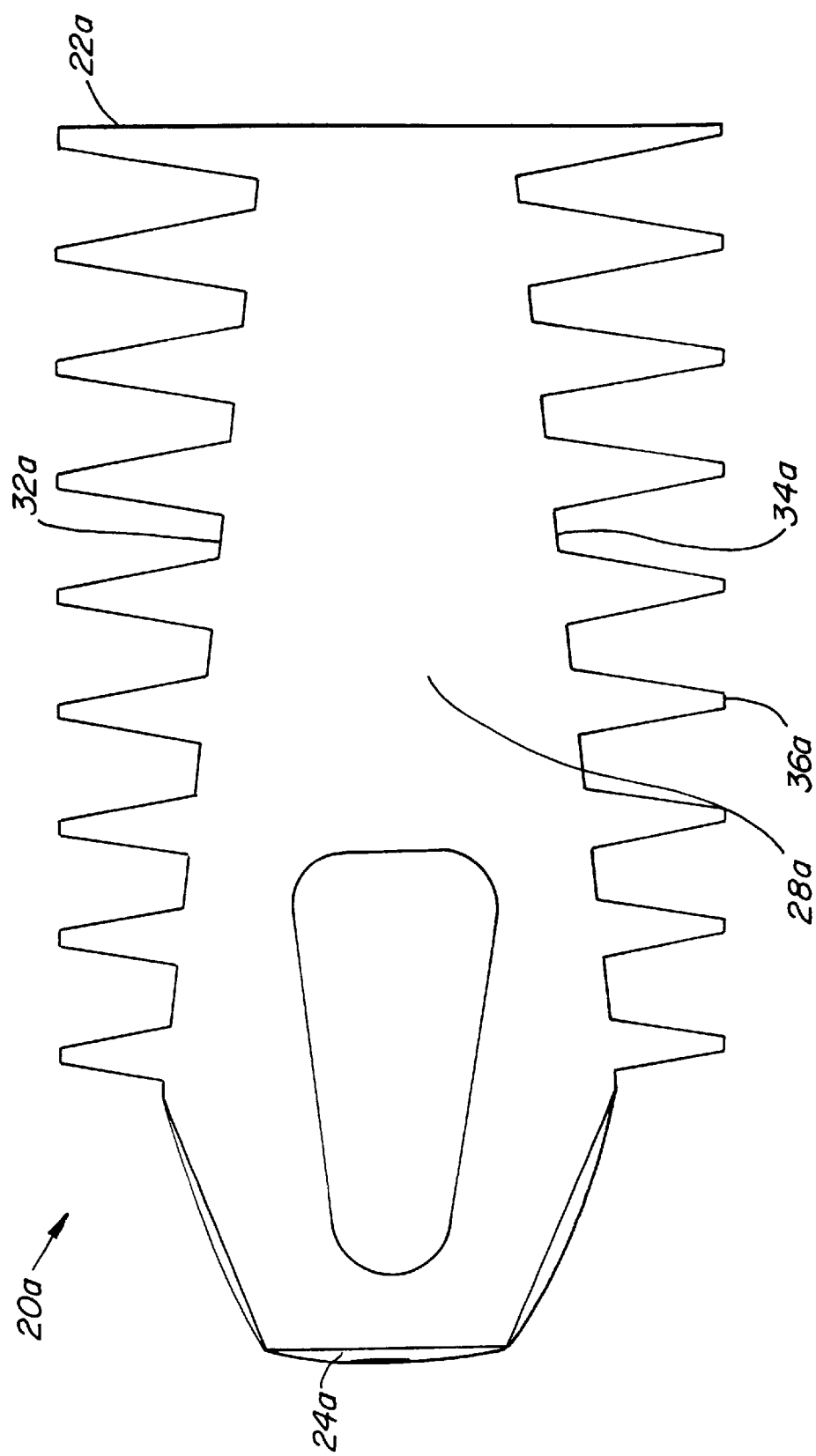
FIG. 18 is a side elevation view of another embodiment of the present insert.
Figure 19:
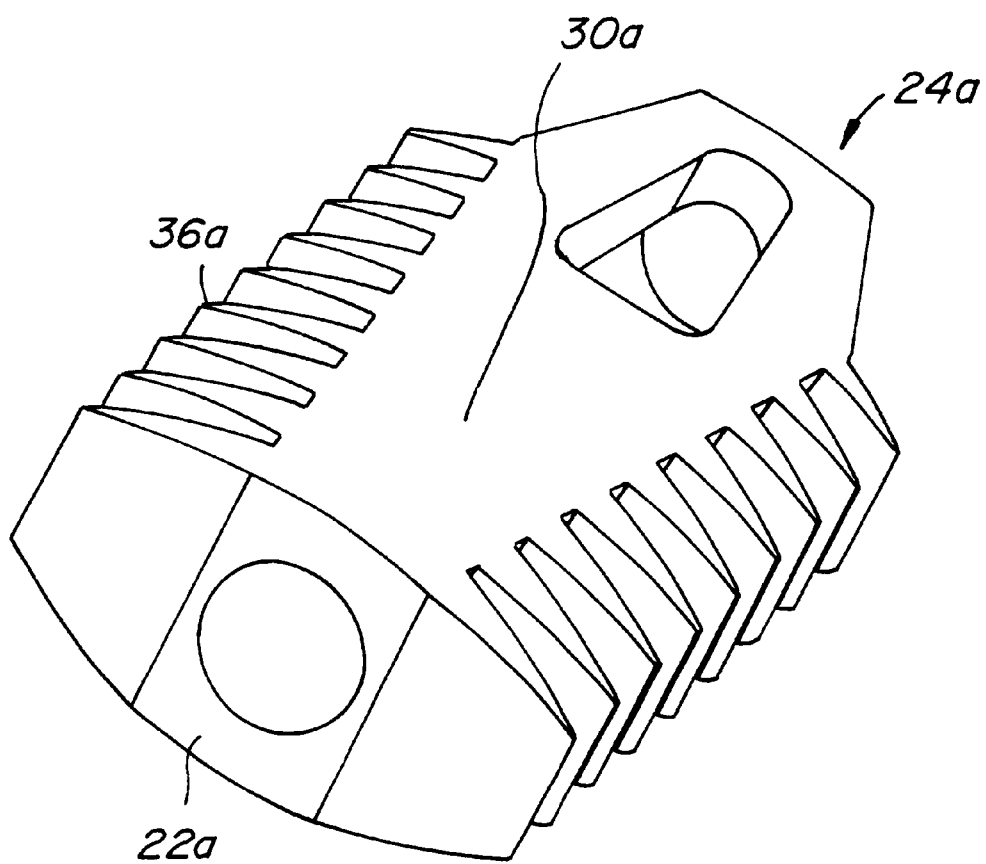
FIG. 19 is a perspective view of the insert of FIG. 18.
Figure 20:
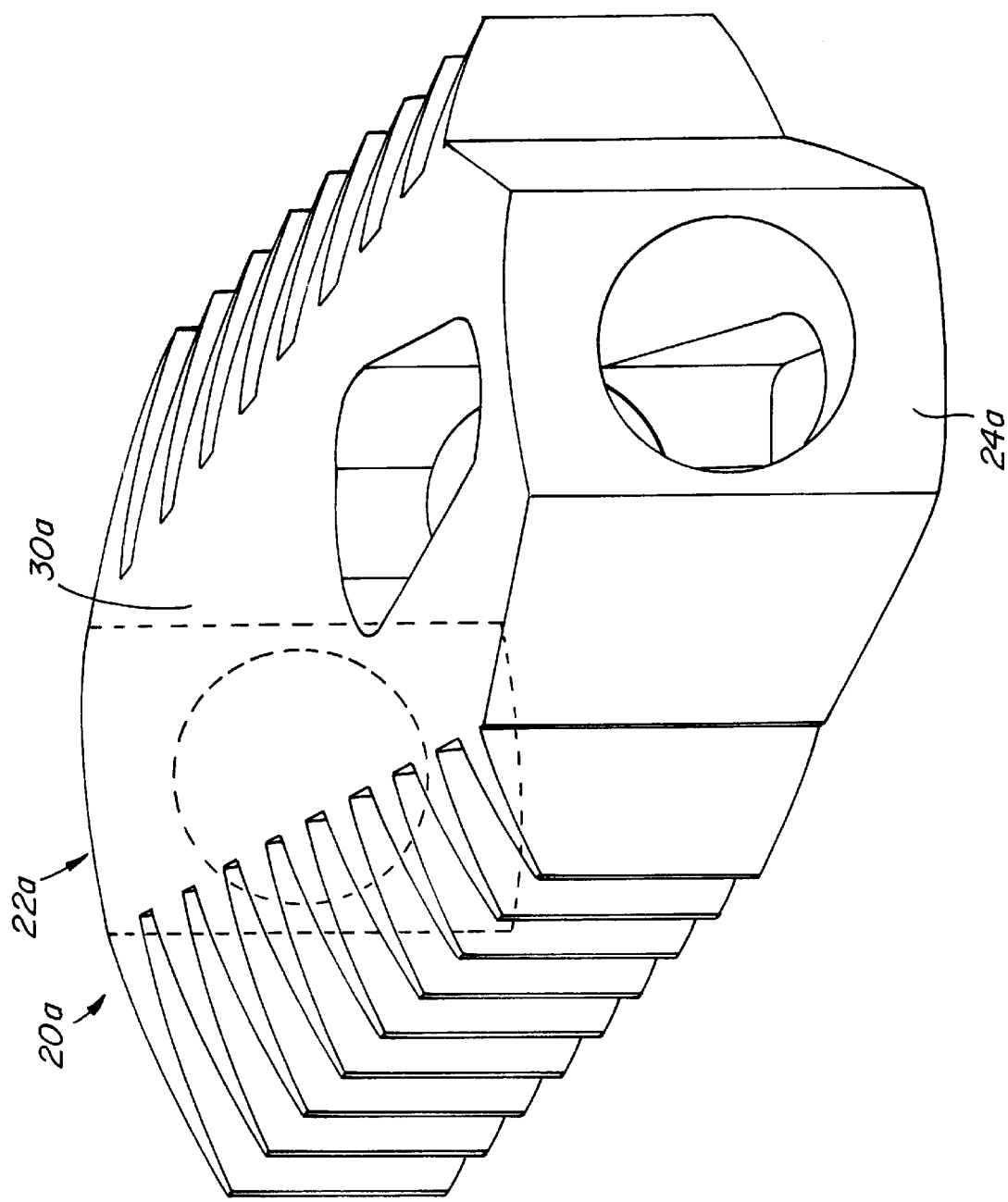
FIG. 20 is a perspective view of the insert of FIG. 18.
Figure 21:
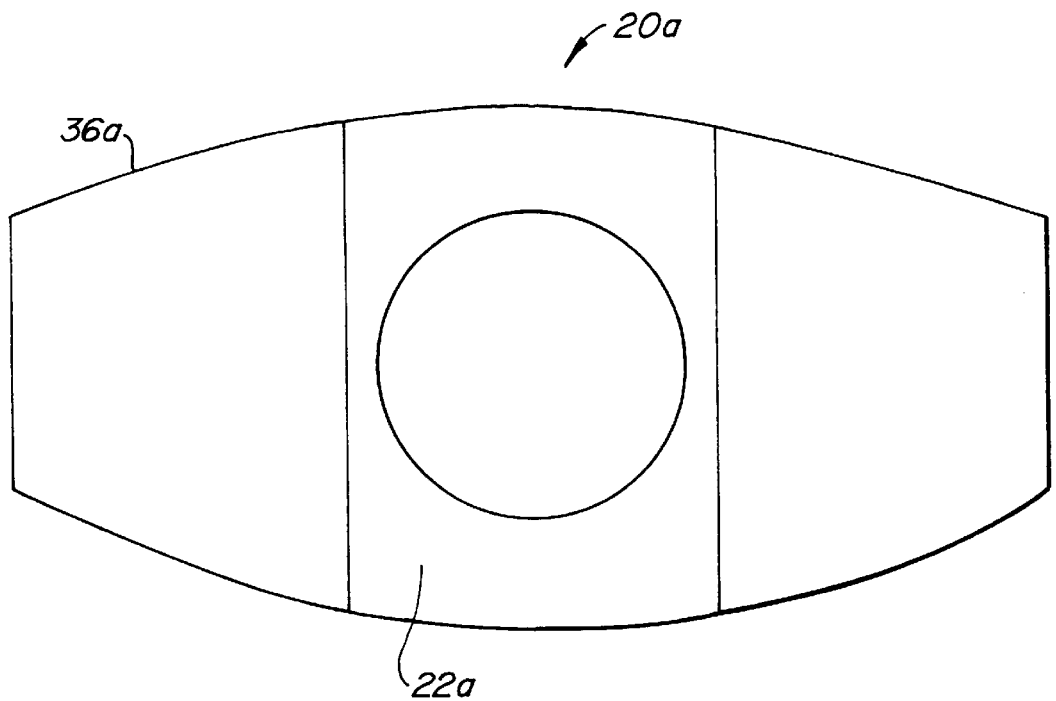
FIG. 21 is an end elevation view of the insert of FIG. 18.

Prior to introduction of the insert into cannula 54, a coring device 64 can be inserted to cut through the annulus and remove osteophytes. An example of a coring device is provided in FIG. 17. Coring device 64 has a hollow end chamber 65 and is preferably punched directly into the material to be removed, and then drawn back out of the cannula with the cut out material being held in the coring device's hollow end chamber 65.

Inserts 20, 19 and 21 are preferably rotated into position, (and anchored into position in the case of insert 20) by an elongated positioning rod 48 which can be received into bore 25 in posterior surface 24 of insert 20, as seen in FIG. 8. Rotation of rod 48 causes the insert to rotate about its axis 26 from the position seen in FIG. 11 through to the position seen in FIG. 13.

The optimal vertebral stabilization between any two adjacent vertebrae will be a function of both the initial and desired separation distance between the vertebrae. The initial separation distance will itself be a function of the amount of tissue deterioration in the intervertebral space. Moreover, the optimal vertebral stabilization will be a function of the condition of the discal tissues and the paraspinal tissues surrounding the intervertebral space. The greater the separation distance, the greater the likelihood of a fusion failure. On the other hand, if there is insufficient paraspinal tissue tension after placement, risk is increased that the vertebrae will move with respect to one another.

Accordingly, the selection of the best size of intervertebral insert for a particular application is important. Consequently, a method is provided for determining the appropriate insert size as follows. A torque wrench 37 can be applied to rod 48 such that the amount of torque necessary to cam apart the adjacent vertebral surfaces 50 and 52 can be measured. The optimal torque required will be a function of many factors including initial intervertebral distance, ligament length and compliance and vertebral endplate load characteristics.

Should the torque required to rotate the implant be too great, the implant should be removed and replaced with a smaller sized implant such that the vertebral surfaces are not damaged or distended too far, damaging surrounding tissue during insert implantation. Conversely, should the torque required to rotate the implant into position be too small, the implant should be removed and replaced with a larger sized implant such that the implant can provide proper vertebral separation and stabilization without being loose and thereby more likely to move out of its referred orientation.

The present invention also provides a minimally invasive surgical method for percutaneously introducing an intervertebral insert into a patient's intervertebral space. This method can be carried out with any insert, including, but not limited to, inserts 20, 19, 21 or 23, as described herein. For illustration purposes, FIGS. 9A and 9B show an example of the method as carried out with insert 20.

First, cannula 54 is percutaneously introduced into a patient's back in a posterolateral approach. Secondly, insert 20 is introduced through cannula 54 into an intervertebral space between adjacent vertebrae 50 and 52. The posterolateral approach is preferably in the range of an angle B of 35 to 90 degrees to an anterior-posterior axis 56 through the patient. Most preferably, angle B is about 45 degrees, such as when two inserts are implanted in the same intervertebral space at an angle to one another, as will be described in conjunction with an additional preferred method. The present angled posterolateral approach has the important advantage that introduction of the implant into the intervertebral space avoids damage to the anterior and posterior longitudinal ligaments, (57 and 59, respectively), the interspinous ligaments and the facet joint capsules.

Cannula 54 preferably has a non-symmetrical passage therethrough which can include an oval or racetrack passage which accommodates the dimensions of surfaces 28 and 30 of insert 20 such that insert 20 is prevented from rotating while it is in the cannula, enabling the insert to be positioned in the intervertebral space in the desired orientation. Another important advantage of cannula 54 having an oval or racetrack shape is that it provides minimal tissue displacement and damage entering into the patient's body as compared to what would be the case if a larger round cannula were used.

Figure 10:
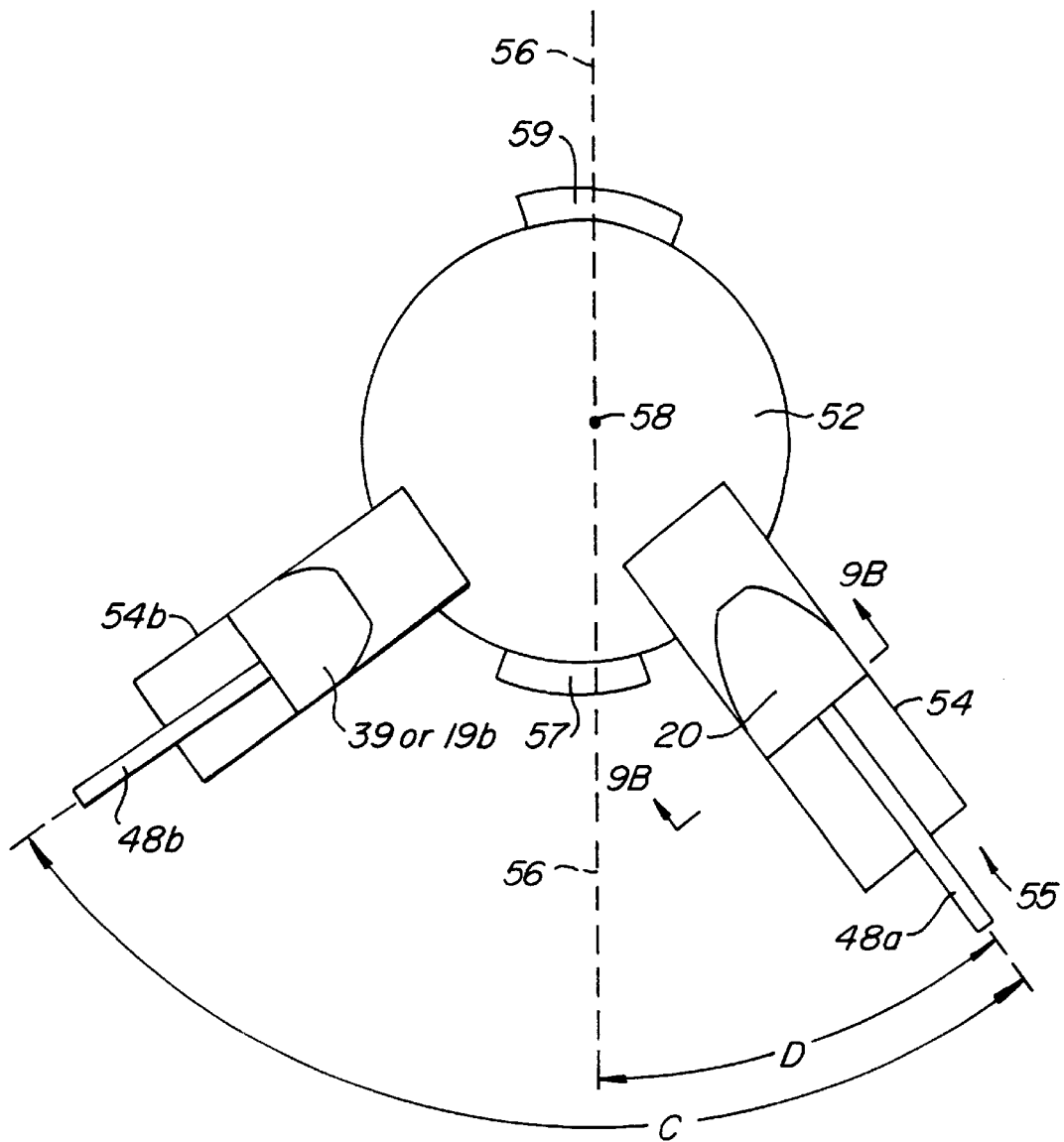
FIG. 10 is a top plan view of 2 cannulae accessing a patient's spinal region.
Figure 14:
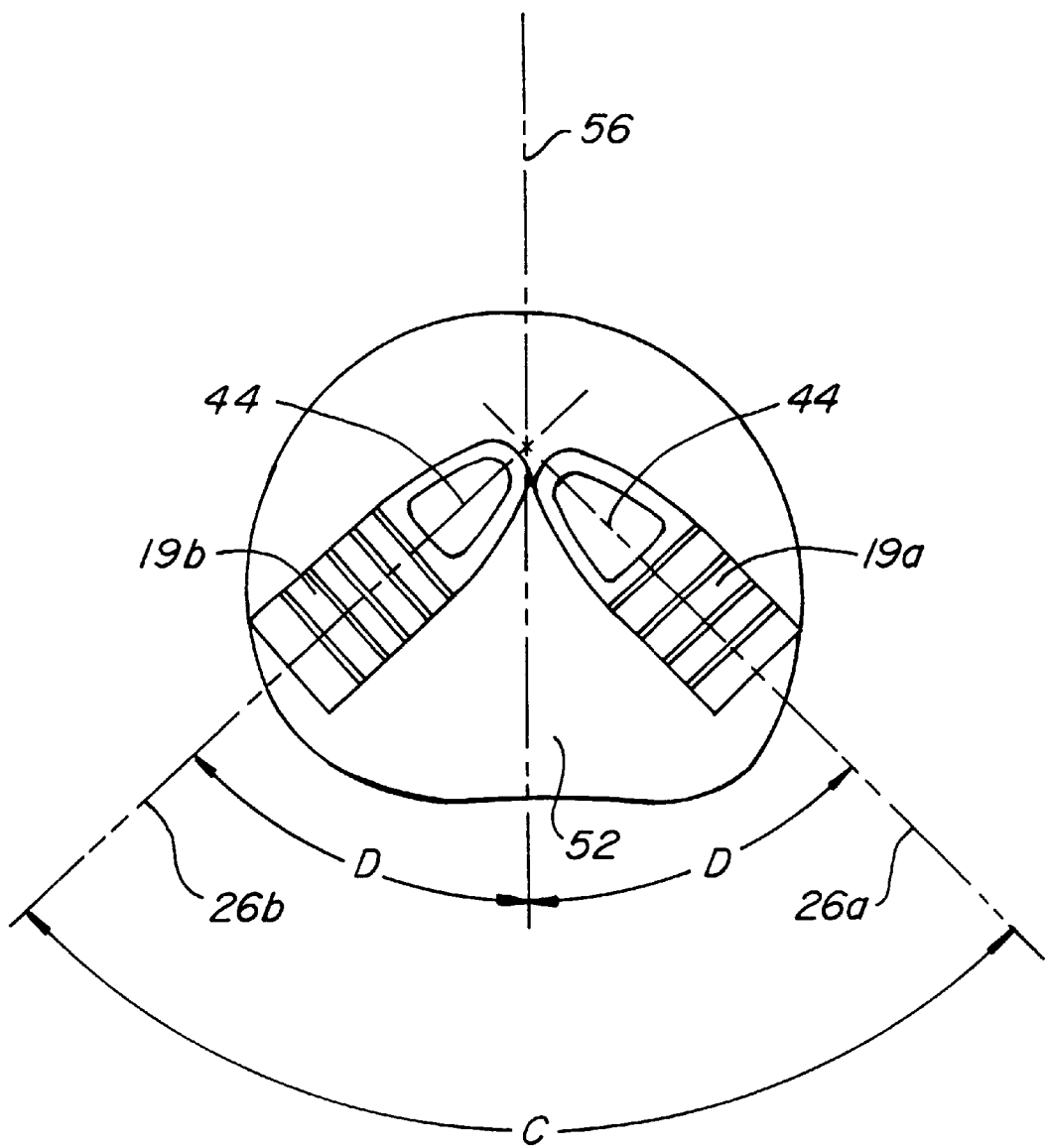
FIG. 14 is a top plan view of a pair of inserts positioned between adjacent vertebrae.

In yet another aspect of the present invention, a method of positioning laterally-spaced apart first and second inserts in a patient's intervertebral space is provided. Preferably, the inserts are oriented at an angle to one another so as to provide increased vertebral stability. This method can be carried out with any intervertebral insert, including, but not limited to, inserts 20, 19, 21 or 23, as described herein. For illustration purposes, FIGS. 10 and 14 show an example of the method as carried out with a pair of inserts 19 such that the pair of inserts 19a and 19b are introduced between adjacent vertebrae 50 and 52. In a preferred aspect of the method, a first insert 19a is inserted between adjacent vertebrae 50 and 52 and then rotated and anchored into position. Following this, a second insert 19b is inserted between adjacent vertebrae 50 and 52 and then rotated and anchored into position. The rotation of the second insert 19b into position will provide additional support to the adjacent vertebrae 50 and 52.

In this preferred method, inserts 19a and 19b are positioned side-by-side between the adjacent vertebrae with the inserts being positioned at an angle C to one another in a laterally spaced-apart orientation, as shown. The advantage of positioning inserts 19a and 19b at an angle to one another is the increased stability between vertebrae 50 and 52 caused by having rotational axes 26a and 26b disposed at angle C to one another. Preferably, angle C will be in the range of 70 to 135 degrees, and most preferably be about 90 degrees. As can be seen in FIG. 10, inserts 19a and 19b are therefore each preferably posterolaterally percutaneously introduced at an angle D being in the range of 35 to 90 degrees, and most preferably 45 degrees, from an anterior-posterior axis 56 passing through the patient's sagittal plane Anterior-posterior axis 56 is perpendicular to spinal axis 58.

As can be seen therefore, only two cannulae 54a and 54b are required to enter through the patient's back when separating and stabilizing vertebrae 50 and 52 by implanting inserts 19a and 19b. As such, a very minimally invasive surgical technique is provided as compared to existing insert systems requiring open posterior techniques. For reasons already set forth, should cannulae 54a and 54b preferably have non-symmetrical cross-sections, the potential for tissue damage is greatly reduced and the ability to position inserts 19a and 19b in the desired orientation within the intervertebral space is greatly enhanced. In this aspect of the method, prior disc distraction with dedicated instrumentation is not required.

In an aspect of this method, as also illustrated in FIG. 10, two posterolaterally introduced percutaneous cannulae 54a and 54b are used to introduce first and second inserts, 19a and 19B, respectively, as set forth above; however, insert 19a is first introduced through cannula 54a concurrently with an instrument 39 being introduced through cannula 54b. Instrument 39 can include a camera or arthroscope for viewing or recording the procedure, articulated forceps, shavers, osteophyte file, vertebral decorticator, oval coring device or bone graft introducer, which can be operated concurrently with the implantation of insert 19a into the patient's intervertebral space. Subsequently, insert 19a is anchored into position by a positioning rod which is then detached from the insert. Instrument 39 is then removed from cannula 54b and introduced into cannula 54a to perform the same function while insert 19b is introduced into the patient's intervertebral space through cannula 54b and anchored into position by a positioning rod which is also then detached.

Important advantages of this method, as distinguished from existing intervertebral systems, include the fact that there is no need in any of the present methods of separating and stabilizing adjacent vertebrae for drilling, chiseling or otherwise coring out large portions of the vertebrae to make way for the insert during the implantation procedure.

Figure 16:
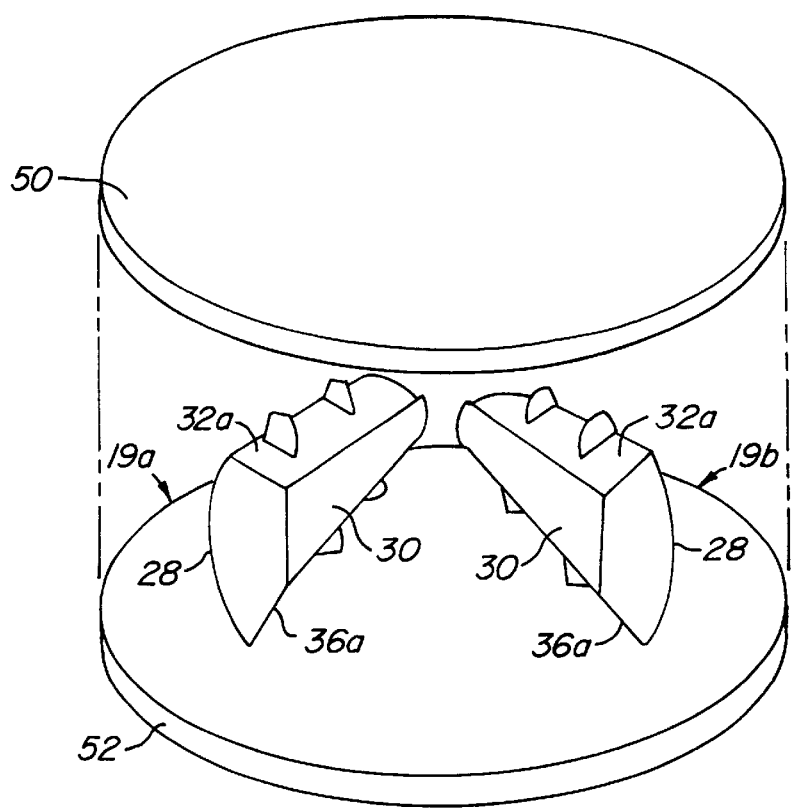
FIG. 16 is an exploded perspective view corresponding to FIG. 14.

As is best seen in FIG. 16, an additional important advantage of using inserts 19a and 19b positioned at right angles to one another is that surfaces 32 and 34 are angled with respect to one another such that they hold vertebrae 50 and 52 apart at a proper lordotic angle, preferably being about 10 degrees. Specifically, inserts 19a and 19b are preferably positioned inverted to one another such that sides 30 oppose one another and sides 28 are positioned towards the rear of the intervertebral space, as shown.

Figure 15:
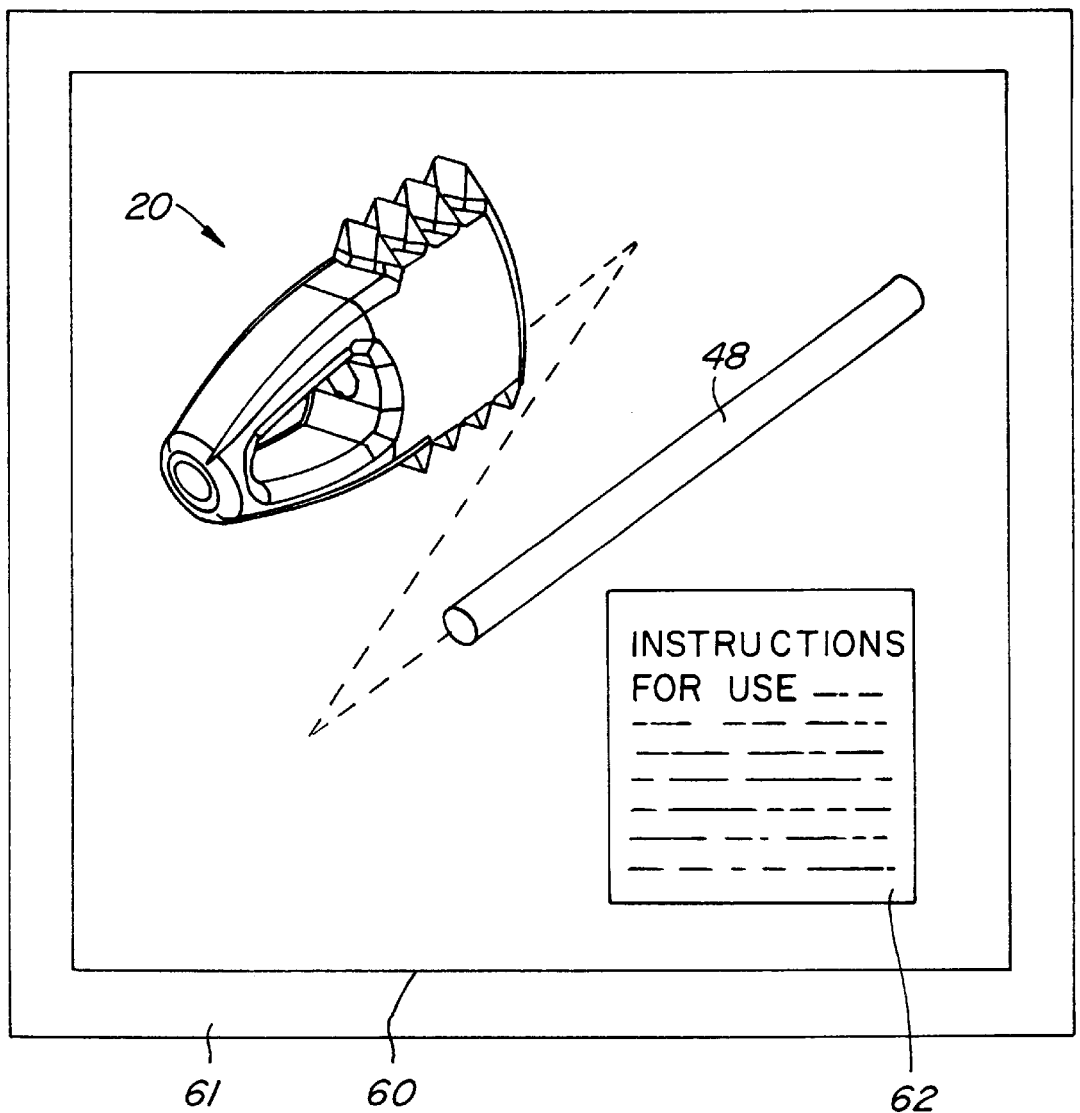
FIG. 15 is a kit comprising an intervertebral insert according to the present invention and instructions for its use.

As is seen in FIG. 15, the present invention also includes a kit 60, which can include intervertebral insert 20. For illustration purposes, insert 20 is shown in FIG. 15. It is to be understood that kit 60 can alternatively include any other intervertebral insert including, but not limited to, inserts 21 and 23 instead or in addition to insert 20. Kit 60 further includes instructions for use 62 which may be in the form of literature accompanying the system, writing on packaging material, information stored on video or audio discs, electromagnetic data storage formats, or other data storage and presentation media. Instructions for use 62 set forth any of the preferred methods described herein. Kits of the present invention may optionally further include a positioning rod as described generally above. The positioning rod can include, but is not limited to, rod 48, as described. The kit components will usually be packaged together in a suitable container 61, such as a pouch, box, tray, tube, or the like, typically being packaged in a sterile condition.

Figure 23:
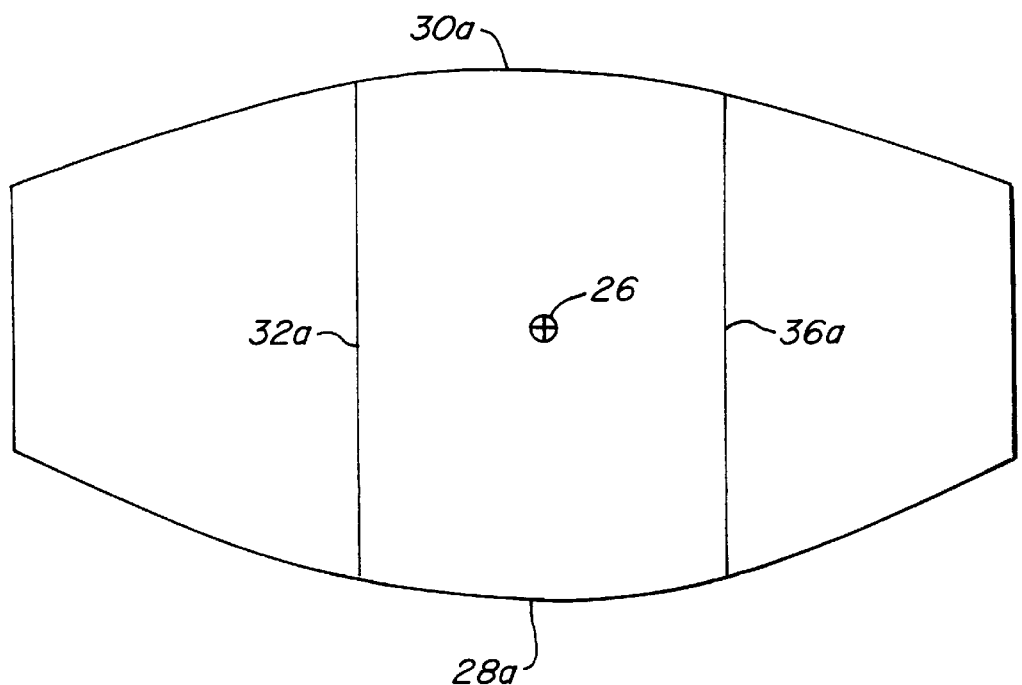
FIG. 23 is a sectional view taken along line 23—23 in FIG. 22.
Figure 22:
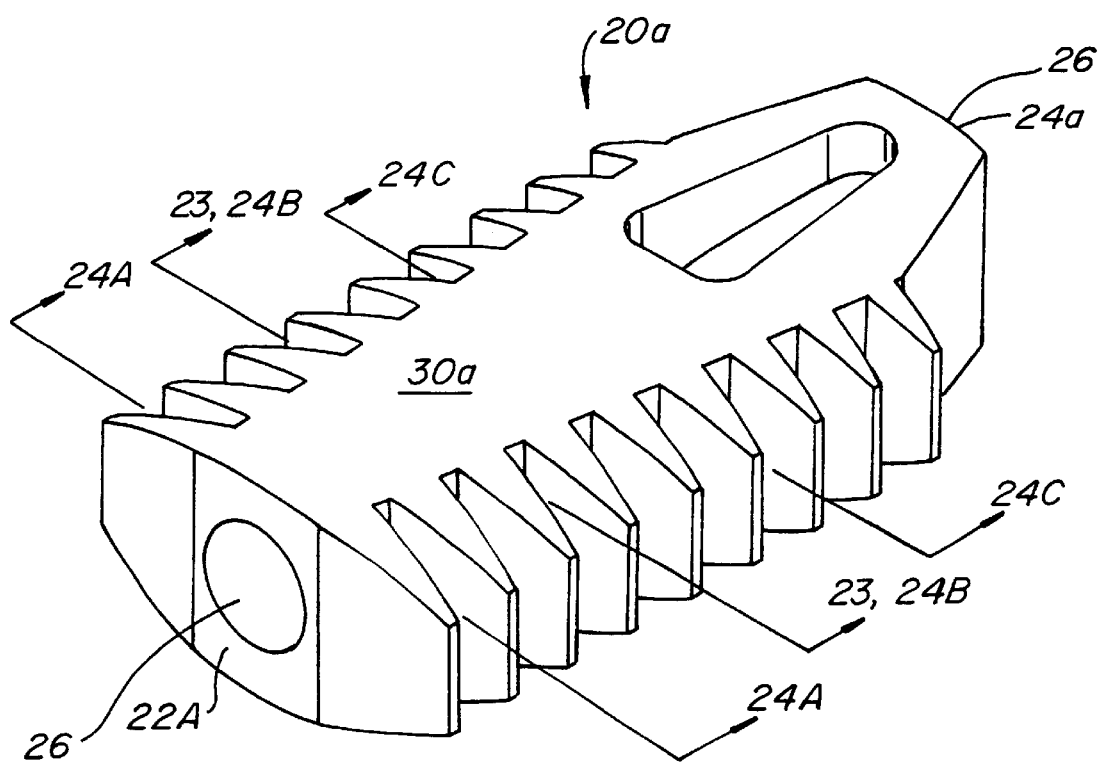
FIG. 22 is a perspective view of the insert of FIG. 18.
Figure 24A:
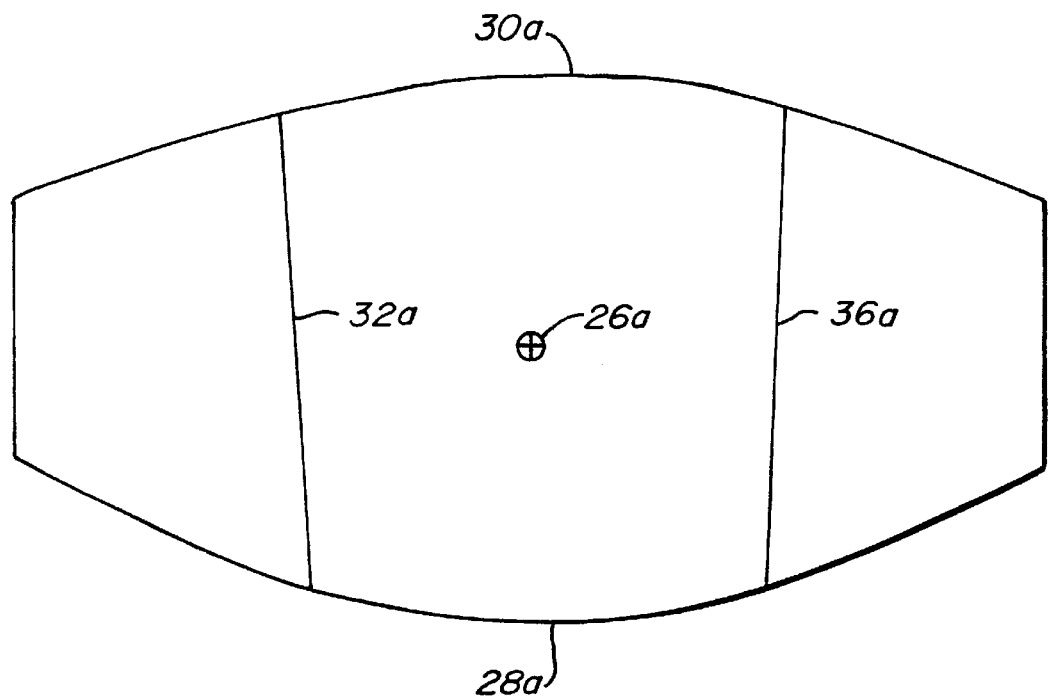
FIGS. 24a, 24b and 24c are views corresponding to FIG. 23, but with but instead having its opposite vertebral supporting surfaces disposed at an angle to one another.

As is shown in FIG. 23, vertebral supporting surfaces 32a and 36a may be disposed generally parallel to one another. However, as is shown in FIGS. 16 and 24a, it is to be understood that vertebral supporting surfaces 32a and 36a may instead be disposed at an angle to one another, as shown, thereby assisting in providing proper intervertebral lordosis.

Figure 24B:
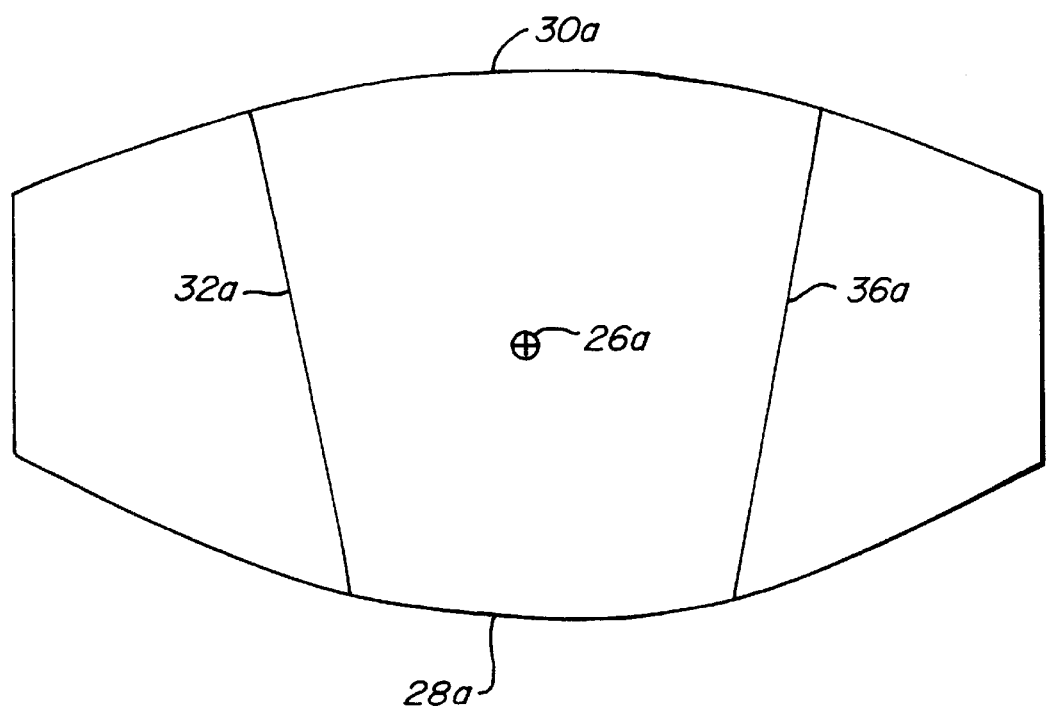
Figure 24C:
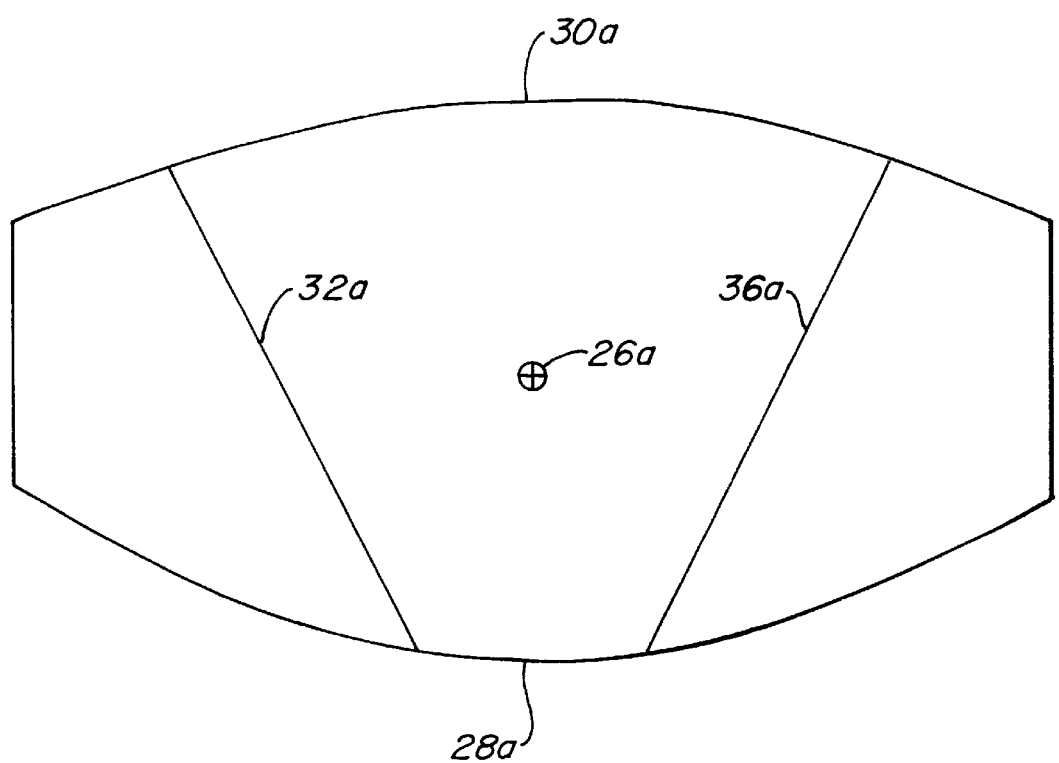

In addition, the angle of surfaces 32a and 36a with respect to one another may be constant from end 22a to 22b of insert 20a. However, as is shown in FIGS. 24a, 24b, and 24c, the angle of surfaces 32a and 36a with respect to one another may instead vary along the length of insert 20a from end 22a to end 24a, also assisting in providing lordosis.

Similarly, with regard to the insert shown in FIG. 4B, it is also to be understood that the angle of surfaces 32 and 36 with respect to one another, may also vary along the length of insert 20 from end 22 to end 24, also assisting in providing lordosis.

Figure 25:
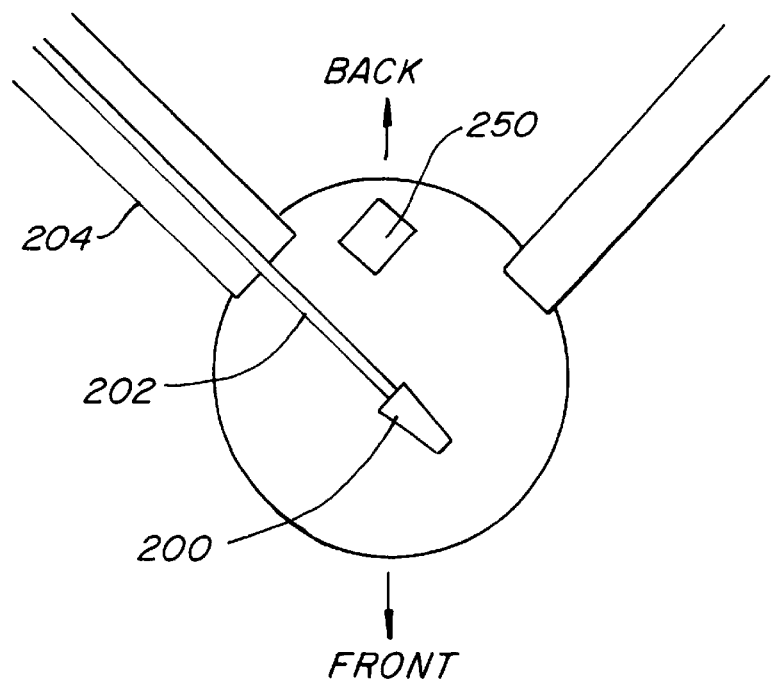
FIG. 25 shows a first step in inserting a quartet of inserts.
Figure 26:
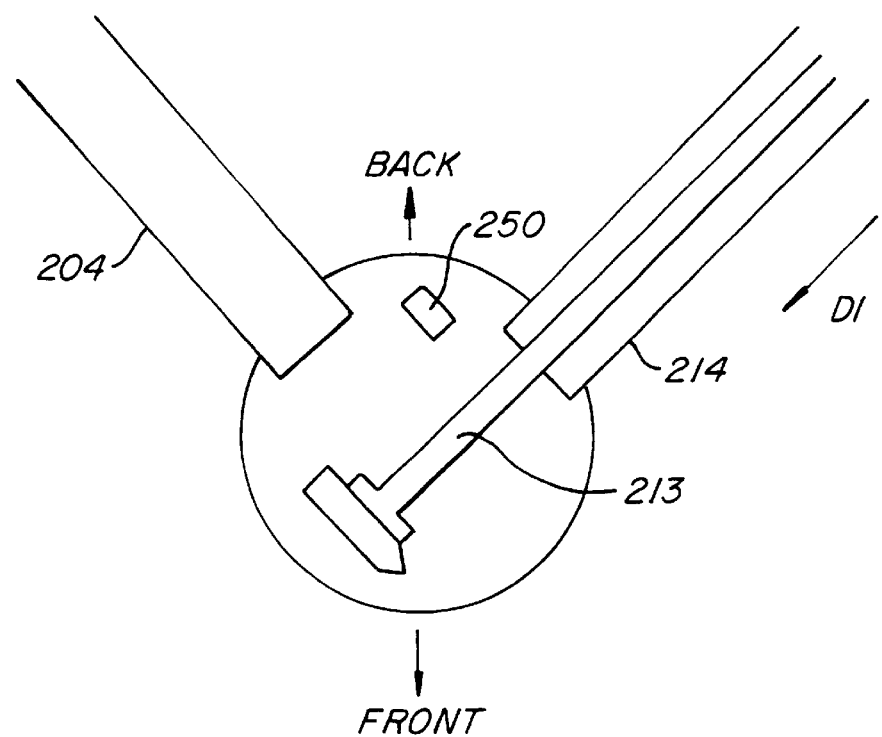
FIG. 26 shows a second step in inserting a quartet of inserts.
Figure 27:
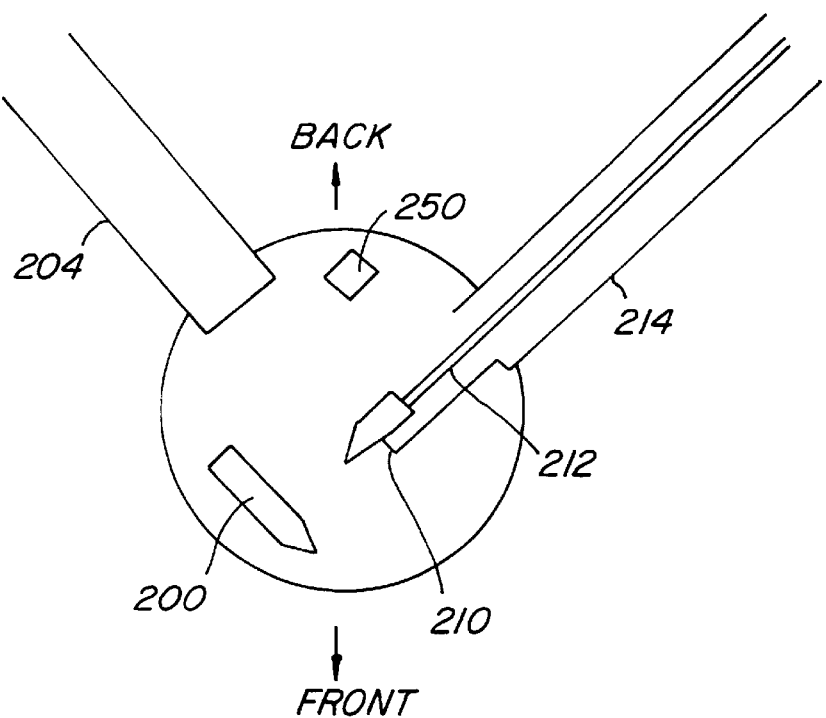
FIG. 27 shows a third step in inserting a quartet of inserts.
Figure 28:
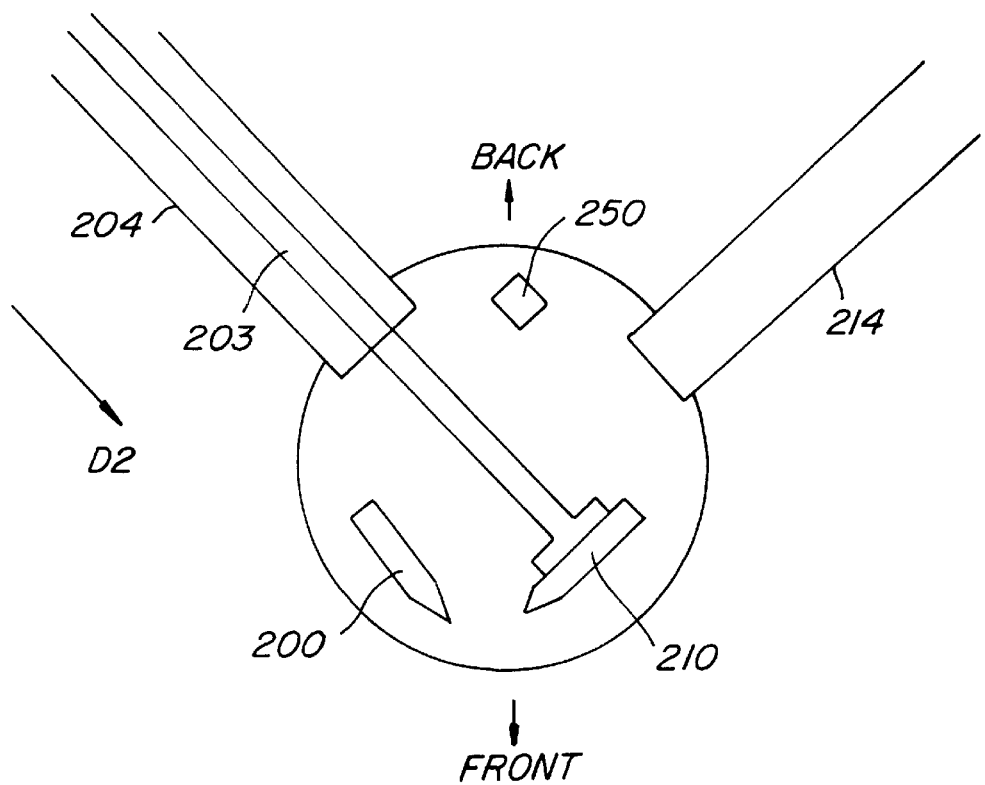
FIG. 28 shows a fourth step in inserting a quartet of inserts.
Figure 29:
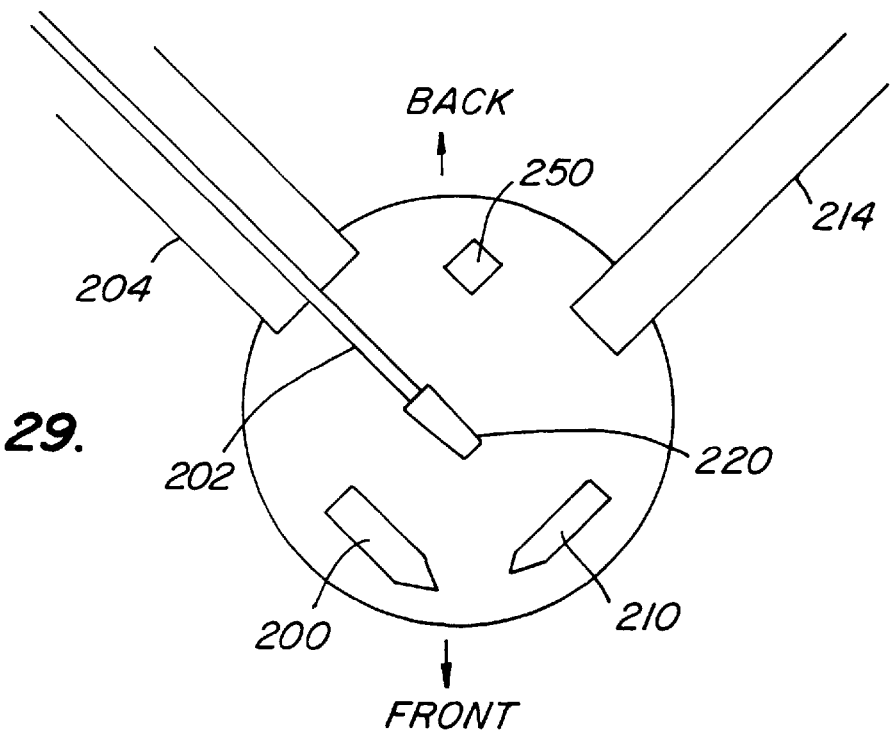
FIG. 29 shows a fifth step in inserting a quartet of inserts.
Figure 30:
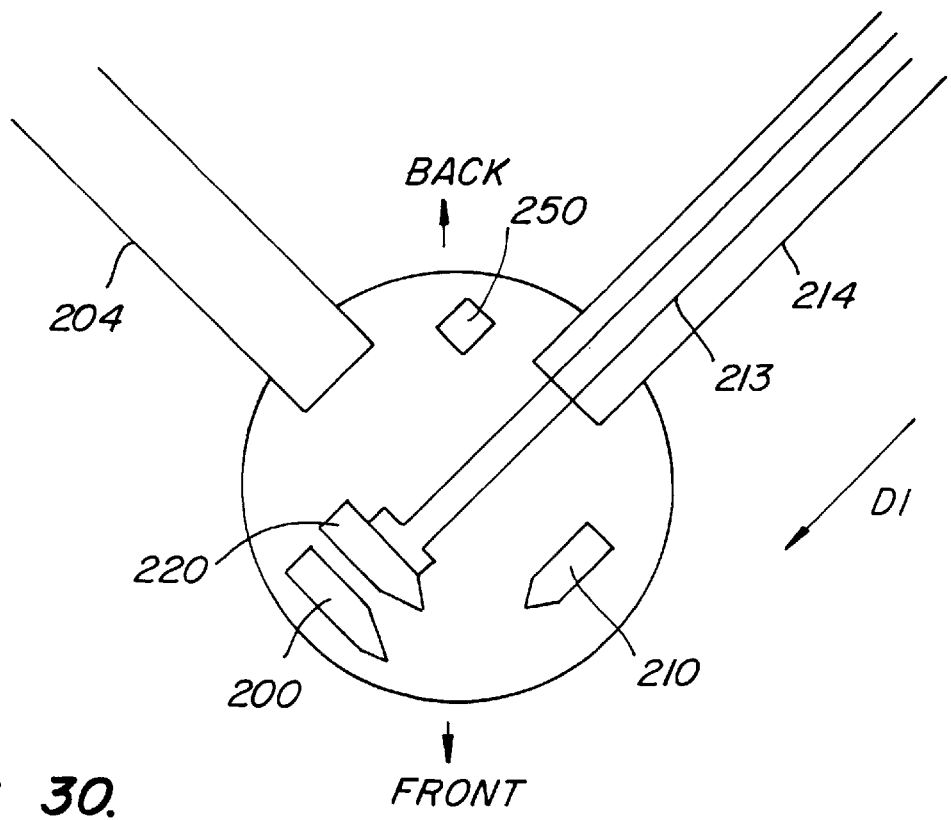
FIG. 30 shows a sixth step in inserting a quartet of inserts.
Figure 31:
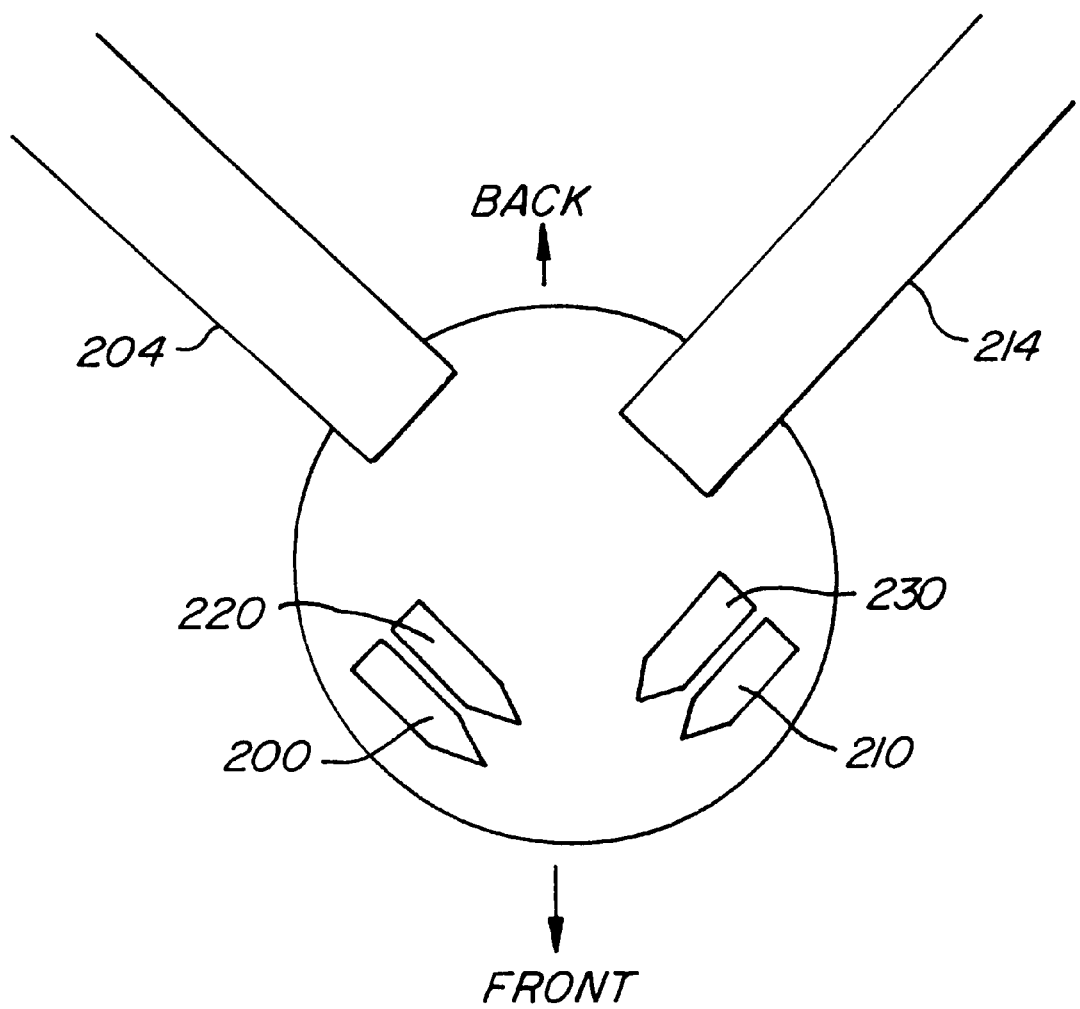
FIG. 31 shows a seventh step in inserting a quartet of inserts.

Increasing numbers of intervertebral inserts will provide an increased surface area for support between the adjacent vertebrae. Accordingly, the present invention also encompasses inserting more than 2 inserts into the patient's intervertebral space, as follows. FIGS. 25 to 31 show sequential steps in inserting a quartet of inserts 200, 210, 220 and 230, as follows. In FIG. 25, a first insert 200 is inserted into a patient's intervertebral space and rotated into position by rod 202 received through cannula 204. Subsequently, as shown in FIG. 26, rod 202 is removed and push rod 213 is inserted through cannula 214, moving insert 200 in direction D1. Subsequently, as shown in FIG. 27, a second insert 210 is inserted into a patient's intervertebral space and rotated into position by rod 212 received through cannula 214. Subsequently, as shown in FIG. 28, rod 212 is removed and push rod 203 is inserted through cannula 204, moving inserter 210 in direction D2. Subsequently, as shown in FIG. 29, a third inserter 220 is inserted into a patient's intervertebral space and rotated into position by rod 202 received through cannula 204. Subsequently, as shown in FIG. 30, rod 202 is removed and push rod 213 is inserted through cannula 214, moving insert 220 in direction D1. Finally, as shown in FIG. 34, a fourth insert 230 is positioned in the patient's intervertebral space using the above described methods. An optional temporary distractor 250 may be positioned in the patient's intervertebral space during the above described procedure to increase the access for sliding inserts 200, 210, 220 and 230 into position.

The illustrations of FIGS. 28 to 34 showing a quartet of inserts 200, 210, 220, and 230 inserted into the patient's intervertebral space is exemplary of the number of inserts which may be inserted into the intervertebral space. As such, more than four inserts, (for example 6, 8, 10 or more), may instead be used. In addition, odd numbers of inserts may be used as well, such as when dealing with non-symmetries in the patient's intervertebral space.

Inserts 200, 210, 220, and 230 may comprise any of inserts 20, 21, 19 and 32 as described herein, however, it may be preferable to use inserts without fins so as to facilitate sliding movement of the inserts in respective D1 and D2 directions.

What is claimed is:

1. A method for separating and stabilizing adjacent vertebrae, the method comprising:
   introducing a first insert between the vertebrae, the first insert having a pair of opposite outwardly facing convexly curved camming surfaces and a pair of opposite generally flattened vertebral support surfaces, and wherein the outwardly facing convexly curved camming surfaces are positioned adjacent the vertebrae; and
   rotating the first insert to engage the outwardly facing convexly curved camming surfaces against the vertebrae to move the vertebrae apart.

2. The method as in claim 1, further comprising anchoring the insert between the vertebrae.

3. The method as in claim 1, wherein the insert is inserted percutaneously.

4. The method as in claim 3, wherein percutaneous insertion of the insert comprises introducing a cannula and introducing the insert therethrough.

5. The method as in claim 3, wherein the cannula has a non-symmetrical passage therethrough.

6. The method as in claim 5, wherein the non-symmetrical passage is oval or racetrack-shaped.

7. The method as in claim 1, further comprising:
   introducing a second insert between the vertebrae, wherein the second insert is laterally spaced apart from the first insert; and
   rotating the second insert to support separation of the adjacent vertebrae.

8. The method as in claim 7, further comprising anchoring the first and second inserts between the vertebrae.

9. The method as in claim 2 or 8, wherein anchoring comprises embedding penetrating elements on the insert into opposed surfaces of the adjacent vertebrae.

10. The method as in claim 9, wherein anchoring comprises rotating the insert until the penetrating elements are fully embedded.

11. The method as in claim 7, wherein the first and second insert are oriented at an angle to one another.

12. The method as in claim 11, wherein the angle is in the range from 70 and 135 degrees.

13. The method as in claim 1, wherein the method is performed without prior distraction of the adjacent vertebrae.

14. The method as in claim 1, wherein the insert is inserted posterolaterally.

15. The method as in claim 1, further comprising measuring the torque required to rotate the implant.

16. The method of claim 1, wherein the outwardly facing convexly curved camming surfaces each have a degree of curvature corresponding to an arc section defined by an angle in the range of 15° to 40°.

17. The method of claim 16, wherein the convexly curved camming surfaces each have a degree of curvature corresponding to an arc section defined by an angle of about 20°.

18. A method of positioning a first and a second insert between adjacent vertebrae along a spinal axis, comprising:
   introducing the first insert between adjacent vertebrae, the first insert having a cross-section having a long axis and a short axis, wherein the first insert is inserted while oriented with its short axis being generally aligned with the spinal axis;
   introducing the second insert between adjacent vertebrae, the second insert having a cross-section having a long axis and a short axis, wherein the second insert is inserted while oriented with its short axis being generally aligned with the spinal axis; wherein the first insert and second insert are oriented at opposite posterolateral angles to one another.

19. The method of positioning a first and a second insert between adjacent vertebrae, as in claim 18, wherein the inserts are inserted percutaneously.

20. The method of positioning a first and a second insert between adjacent vertebrae, as in claim 19, wherein precutaneous insertion of the insert comprise introducing the first insert through a first cannula and introducing the second insert through a second cannula.

21. The method of positioning a first and a second insert between adjacent vertebrae, as in claim 20, wherein the cannulae have a non-symmetrical passage therethrough.

22. The method of positioning a first and a second insert between adjacent vertebrae, as in claim 18, wherein the inserts are inserted posterolaterally.

23. The method of positioning a first and a second insert between adjacent vertebrae, as in claim 18, further comprising, rotating the first insert such that cam surfaces of the first insert separates the adjacent vertebrae; and rotating the second insert such that cam surfaces of the second insert separates the adjacent vertebrae.

24. The method of positioning an insert between adjacent vertebrae, as in claim 18, wherein the angle is in the range from 70 to 180 degrees.

25. A method for inserting a plurality of inserts in a patient's intervertebral space, comprising:

advancing a first insert through a first cannula into the intervertebral space;

rotating the first insert, thereby positioning the first insert between adjacent vertebrae;

advancing a first push rod through a second cannula to move the first insert away from the distal end of the first cannula;

advancing a second insert through the second cannula into the intervertebral space;

rotating the second inserter; and advancing a second push rod through the first cannula to move the second insert in an direction away from a distal end of the second cannula.

26. The method of claim 25, wherein, the directions away from the distal ends of the first and second cannulae are anterior directions.

27. The method of claim 25, further comprising:

advancing a third insert through the first cannula into the intervertebral space;

rotating the third insert, thereby positioning the third insert between adjacent vertebrae; and advancing the first push rod through the second cannula to move the third insert away from the distal end of the first cannula.

28. The method of claim 25, further comprising:

advancing a fourth insert through the second cannula into the intervertebral space;

rotating the fourth insert, thereby positioning the fourth insert between adjacent vertebrae; and advancing the second push rod through the first cannula to move the fourth insert away from the distal end of the second cannula.

* * * * *